US009233949B2

(12) United States Patent
Brown et al.

(10) Patent No.: US 9,233,949 B2
(45) Date of Patent: Jan. 12, 2016

(54) TREATMENT FOR OXIDATIVE STRESS AND/OR HYPERTENSION

(75) Inventors: Milton L. Brown, Brookeville, MD (US); Yali Kong, Centreville, VA (US); Christopher Stuart Wilcox, Washington, DC (US)

(73) Assignee: Georgetown University, Washington, DC (US)

( * ) Notice: Subject to any disclaimer, the term of this patent is extended or adjusted under 35 U.S.C. 154(b) by 696 days.

(21) Appl. No.: 13/395,764

(22) PCT Filed: Sep. 17, 2010

(86) PCT No.: PCT/US2010/049260
§ 371 (c)(1),
(2), (4) Date: Apr. 18, 2012

(87) PCT Pub. No.: WO2011/035110
PCT Pub. Date: Mar. 24, 2011

(65) Prior Publication Data
US 2012/0196896 A1    Aug. 2, 2012

Related U.S. Application Data

(60) Provisional application No. 61/243,677, filed on Sep. 18, 2009.

(51) Int. Cl.
| C07D 401/14 | (2006.01) |
| A61K 31/4184 | (2006.01) |
| A61K 31/45 | (2006.01) |
| A61K 31/416 | (2006.01) |
| A61K 31/454 | (2006.01) |
| A61K 45/06 | (2006.01) |

(52) U.S. Cl.
CPC ............ *C07D 401/14* (2013.01); *A61K 31/416* (2013.01); *A61K 31/4184* (2013.01); *A61K 31/45* (2013.01); *A61K 31/454* (2013.01); *A61K 45/06* (2013.01)

(58) Field of Classification Search
CPC .............................. C07D 401/04; C07D 401/14
USPC ................................... 546/199; 514/322, 315
See application file for complete search history.

(56) References Cited

U.S. PATENT DOCUMENTS

| 5,591,762 A | 1/1997 | Hauel et al. | |
| 6,358,986 B1* | 3/2002 | Schneider | 514/394 |
| 2006/0046967 A1* | 3/2006 | Satyam | 514/19 |

FOREIGN PATENT DOCUMENTS

| WO | WO-2009/094242 A1 | 7/2009 |
| WO | WO-2009/106471 A2 | 9/2009 |

OTHER PUBLICATIONS

Arun et al Journal of Hypertension 2004, 22, 2143-2152.*

(Continued)

*Primary Examiner* — Celia Chang
(74) *Attorney, Agent, or Firm* — Alan W. Steele; Foley Hoag LLP

(57) ABSTRACT

One aspect of the invention relates to compounds, compositions and methods for treating oxidative stress and/or hypertension. In certain embodiments, the invention relates to a mixture of tempol and an angiotensin receptor blocker (ARB) and the use of said mixture to treat oxidative stress and/or hypertension. In certain embodiments, the invention relates to a tempol/ARB adduct and the use of said adduct to treat oxidative stress and/or hypertension.

5 Claims, 8 Drawing Sheets

(56) References Cited

OTHER PUBLICATIONS

Patel et al Am J Physiol Regul Integr Com Physiol 2005, 290, R37-R43.*
Fuchs et al Free Radical Biology and Medicine 1993, 15, 415-423.*
Elmarakby et al. "NADPH oxidase inhi . . . " Hypertension 45 p. 283-87 (2005).*
Wienei et al. "A review on telmi . . . " Cardiovas. Drugs rev. 18(2) 127-154 (2000).*
Wilcox et al. "Chemistry and antihyper . . . " Pharmacol. Rev. 60(4)418-469 (2008).*

Ishiguro, N. et al., "Establishment of a Set of Double Transfectants Coexpressing Organic Anion Transporting Polypeptide 1B3 and Hepatic Efflux Transporters fro the Characterization of teh Hepatobiliary Transport of Telmisartan Acylglucuronide", *Drug Metabolism and Deposition*, 36(4):796-805 (The American Society for Pharmacology and Experimental Therapeutics, USA, 2008).
Extended European Search Report from corresponding European regional application EP 10817885.6 dated Mar. 4, 2013.
International Search Report and Written Opinion from corresponding PCT application PCT/US2010/049260 dated May 26, 2011.

* cited by examiner

Figure 8

| Drug | Duration (hour) | Salt Intake | Number | MAP (before, mmHg) | MAP (after, mmHg) | HR (before, min$^{-1}$) | HR (after, min$^{-1}$) |
|---|---|---|---|---|---|---|---|
| Vehicle | 16-24 | Normal | 8 | 144 ± 0.7 | 142 ± 0.8 | 305 ± 9 | 301 ± 6 |
| Tempol | | | 6 | 144 ± 0.5 | 141 ± 1.0 | 298 ± 3 | 294 ± 3 |
| Telmisartan | | | 6 | 143 ± 0.7 | 113 ± 1.0 | 302 ± 6 | 302 ± 1 |
| Tempol + Telmisartan | | | 6 | 146 ± 0.7 | 119 ± 1.5 | 301 ± 11 | 299 ± 0 |
| Temposartan | | | 5 | 143 ± 0.6 | 119 ± 0.9 | 300 ± 7 | 300 ± 1 |
| Vehicle | 16-24 | High | 7 | 150 ± 0.7 | 148 ± 0.9 | 312 ± 8 | 311 ± 8 |
| Tempol | | | 6 | 152 ± 0.9 | 138 ± 0.3 | 315 ± 6 | 310 ± 9 |
| Telmisartan | | | 6 | 150 ± 0.6 | 127 ± 0.7 | 311 ± 8 | 310 ± 1 |
| Tempol + Telmisartan | | | 6 | 149 ± 0.9 | 115 ± 1.8 | 312 ± 5 | 307 ± 8 |
| Temposartan | | | 6 | 150 ± 0.5 | 123 ± 0.6 | 310 ± 6 | 309 ± 2 |
| Candesartan | | | 6 | 150 ± 1.0 | 130 ± 1.0 | 313 ± 5 | 311 ± 6 |
| Tempol + Candesartan | | | 6 | 151 ± 0.8 | 126 ± 1.0 | 312 ± 6 | 309 ± 3 |
| Vehicle | 88-96 | High | 7 | 153 ± 0.5 | 153 ± 0.4 | 318 ± 5 | 314 ± 3 |
| Tempol | | | 6 | 150 ± 0.7 | 137 ± 0.5 | 311 ± 6 | 307 ± 7 |
| Telmisartan | | | 6 | 150 ± 0.6 | 123 ± 0.9 | 316 ± 5 | 309 ± 5 |
| Tempol + Telmisartan | | | 6 | 152 ± 0.8 | 123 ± 1.0 | 314 ± 6 | 310 ± 6 |
| Temposartan | | | 6 | 152 ± 0.8 | 121 ± 0.9 | 316 ± 3 | 303 ± 4 |
| Candesartan | | | 6 | 150 ± 1.0 | 129 ± 0.8 | 315 ± 4 | 311 ± 5 |
| Tempol + Candesartan | | | 6 | 151 ± 0.8 | 127 ± 0.9 | 316 ± 5 | 310 ± 6 |

TREATMENT FOR OXIDATIVE STRESS AND/OR HYPERTENSION

RELATED APPLICATIONS

This application is the U.S. national phase of international patent application Serial No. PCT/US2010/049260, filed Sep. 17, 2010, which claims the benefit of priority to U.S. Provisional Patent Application No. 61/243,677, filed Sep. 18, 2009.

GOVERNMENT SUPPORT

This invention was made with government support under DK-36079, DK-49870, and HL-68686 awarded by the National Institutes of Health. The government has certain rights in the invention.

BACKGROUND

Current guidelines for the treatment of hypertension recommend an angiotensin receptor blocker (ARB) or an angiotensin-converting enzyme inhibitor (ACEI) as first- or second-line therapy according to subject characteristics and comorbid conditions (23).

ARBs lower the blood pressure of subjects with established hypertension or prehypertension (17). They reduce cardiovascular risk of stroke (51), myocardial infarction in heart failure (10, 26) and overall cardiovascular events in high risk individuals (20, 54) and improve coronary microcirculation and insulin resistance among subjects with hypertension and left ventricular hypertrophy (13). ARBs reduce proteinuria and slow the progressive loss of kidney function in subjects with nephropathy due to type 2 diabetes mellitus (7, 36). They are recommended as first- or second-line therapy for hypertension (8).

Among ARBs, telmisartan is distinguished by its lipophilicity, prolonged duration of action and additional activity as a peroxisome proliferator activated receptors gamma (PPARγ) agonist (5, 6, 14). The PPARγ activity of telmisartan is independent of its angiotensin type 1 receptor (AT1-R) blocking action (41). Candesartan also is a long-duration ARB but lacks significant PPARγ agonist action (41). Moreover, telmisartan is more effective than losartan in reducing proteinuria in a trial of subjects with diabetic nephropathy (4).

The limits of benefit by renin system intervention may have been reached with current ACEIs and ARBs because combination therapy does not appear to provide further protection against myocardial infarction and heart events and was achieved at the cost of increased adverse events (27, 54). However, antihypertensive therapy fails to abolish the cumulative risk of hypertension or cardiovascular disease, especially in elderly subjects, and those with comorbid conditions (1, 2). Moreover, a high salt intake that is characteristic of the modern diet reduces the antihypertensive and antiproteinuric effects of ACEIs or ARBs and thereby limits the potential of single agent therapies. This has spurred the search for other targets in addition to those directly stimulated through angiotensin II (Ang II) generation and activation of the AT1-R. These include enhanced signaling by endothelin type A and B receptors (18), adrenergic receptors (21, 22), thromboxane prostanoid receptors (47, 49) and diminished PPARγ activity (32). Of interest, all of these activating processes raise blood pressure (BP), engage oxidative stress and increase the generation of superoxide anion ($O_2.^-$) in animals and/or vascular smooth muscle cells in culture (32, 48). This provides a rationale for the use of an effective antioxidant to enhance the efficacy of drugs that block the renin-angiotensin-aldosterone (RAA) system.

SUMMARY OF THE INVENTION

One aspect of the invention relates to a mixture of tempol and an ARB, such as telmisartan or candesartan, or a tempol/ARB adduct, such as a tempol/telmisartan ester-linked adduct ("YK" or "temposartan") or a tempamine/telmisartan amide-linked adduct ("PLJ" or "tempamsartan"), and the use of said mixture or adduct to treat oxidative stress and/or hypertension, by reducing Ang II-stimulated vascular superoxide ($O_2.^-$) and blood pressure (BP).

As described herein, the effects of tempol, telmisartan, tempol in combination with telmisartan ("tempol+telmisartan"), and a tempol/telmisartan ester-linked adduct ("YK" or "temposartan") or similar, ester-linked adducts between tempol and other ARBs such as candesartan were compared on radioligand displacement assays, superoxide dismutase (SOD) mimetic activity assays, superoxide ($O_2.^-$) generation assays (by Ang II-stimulated spontaneously hypertensive rat (SHR) preglomerular vascular smooth muscle cells, preglomerular vascular smooth muscle cells (PGVSMCs), assessed from lucigenin-enhanced chemiluminescence) and mean arterial pressure (MAP) assays (of conscious SHR receiving a high salt diet, assessed telemetrically after gavage for four days with vehicle or 80 μmol·kg$^{-1}$ of drugs).

It was found that telmisartan and tempol/telmisartan ester-linked adduct have similar AT1-receptor ligand displacement activity, whereas tempol and tempol/telmisartan ester-linked adduct have similar SOD mimetic activity. Unlike tempol and tempol/telmisartan ester-linked adduct, telmisartan alone had no intrinsic SOD mimetic activity when tested alone in vitro in an SOD generating medium. All compounds produced dose-dependent reductions in $O_2.^-$ generation in PGVSMCs stimulated with angiotensin II, but the sensitivity to tempol+telmisartan and tempol/telmisartan ester-linked adduct were about 100-fold to about 1.000-fold greater than either compound individually. Each drug reduced MAP significantly over 24 hours, but tempol+telmisartan and tempol/telmisartan ester-linked adduct reduced MAP significantly ($p<0.05$) more than telmisartan or tempol alone. Moreover, the tempol-telmisartan ester-linked adduct reduced MAP significantly more than candesartan or candesartan plus tempol. However, over four days, this additive effect disappeared, although tempol plus telmisartan and the tempol-telmisartan ester-linked adduct still reduced blood pressure more than candesartan or candesartan plus tempol.

Panel C contrasts the responses of spontaneously hypertensive rats to four dose of 80 or 800 μmol kg$^{-1}$ of tempol during a high salt diet (n=6 per study).

Figure 3:
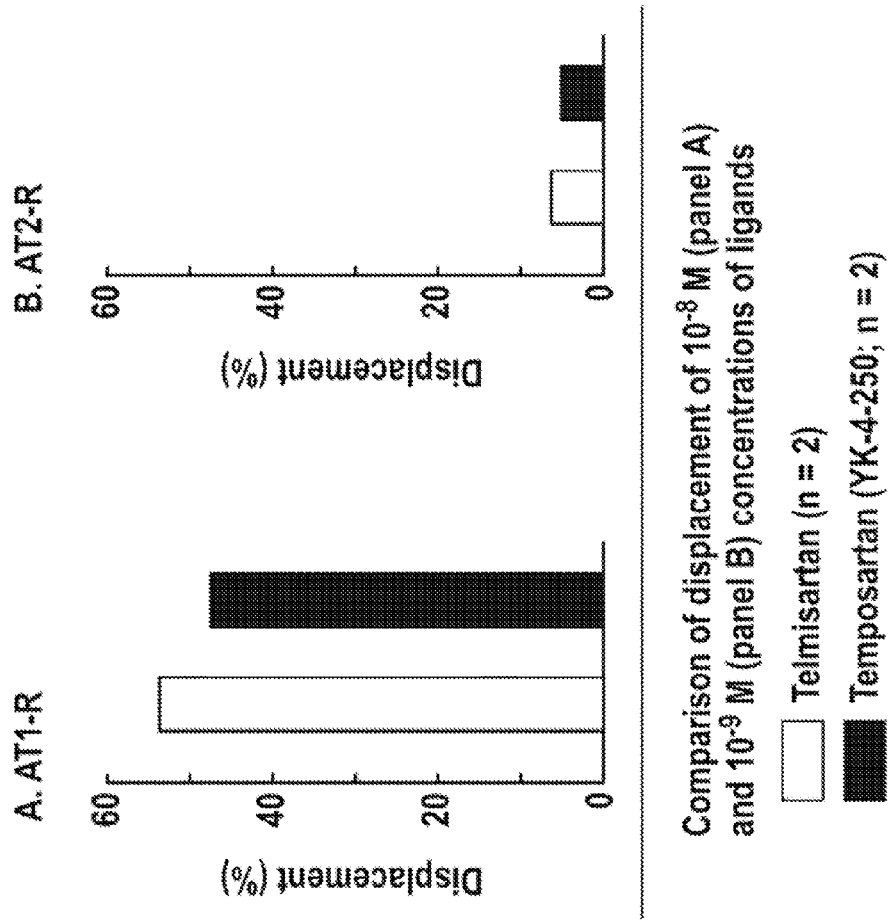

FIG. 3 is a pair of graphs depicting the mean value for displacements of radiolabeled Ang II by telmisartan or tempol/telmisartan ester-linked adduct (YK-4-250). Panel A, displacement of AT1 receptor (AT1-R) bindings at $10^{-9}$ M drug concentration (n=2). Panel B, displacement of Ang II receptor (AT2-R) binding at $10^{-8}$ M drug concentration (n=2).

Figure 4:
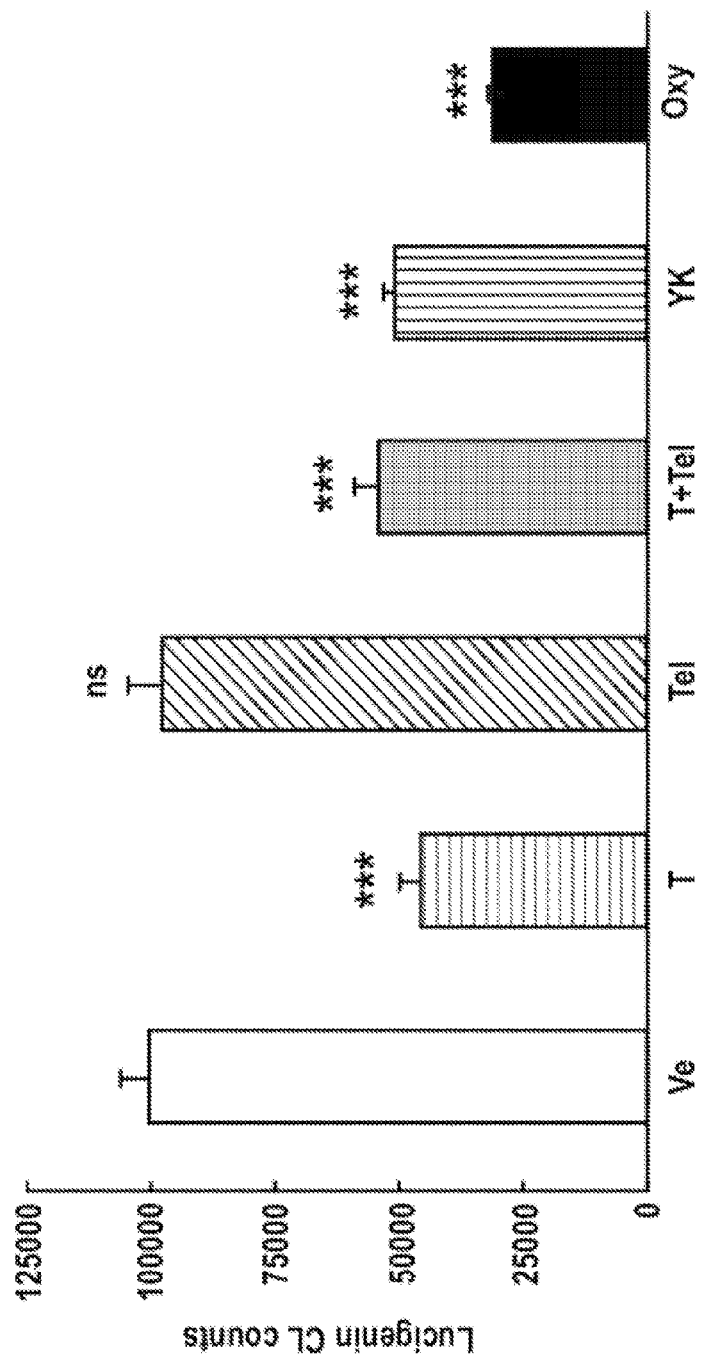

FIG. 4 is a graph depicting Lucigenin-enhanced chemiluminescence (CL) counts in a cell-free system of xanthine+xanthine oxidase after incubation with vehicle (Ve) or in a final concentration of $10^{-4}$ M tempol (T), telmisartan (Tel), T+Tel, tempol/telmisartan ester-linked adduct (YK) or oxypurinol (Oxy). n=3 per group. Compared to vehicle: *, p<0.05; , p<0.01; * p<0.005.

Figure 5:
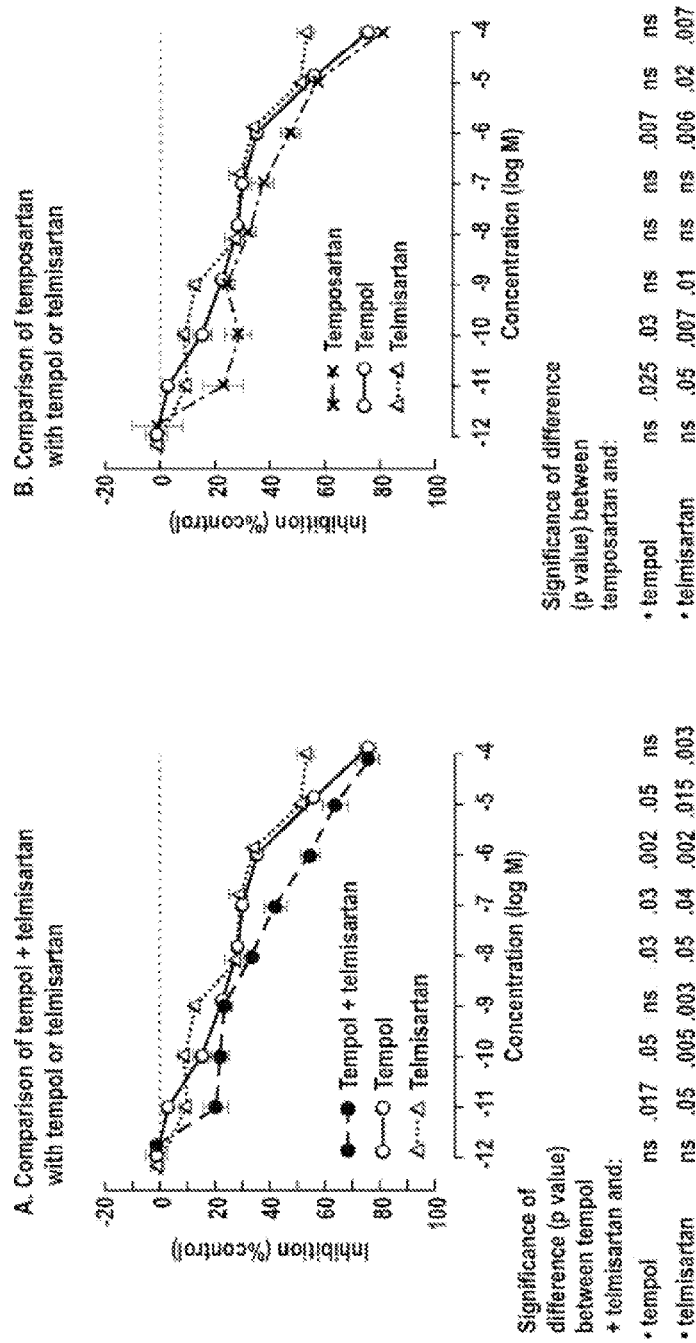

FIG. 5 is a pair of graphs depicting mean±SEM values (n=3) for dose-dependent effects of drugs on lucigenin-enhanced chemiluminescence in Ang II-stimulated spontaneously hypertensive rat preglomerular vascular smooth muscle cells. ns, not significant.

Figure 6:
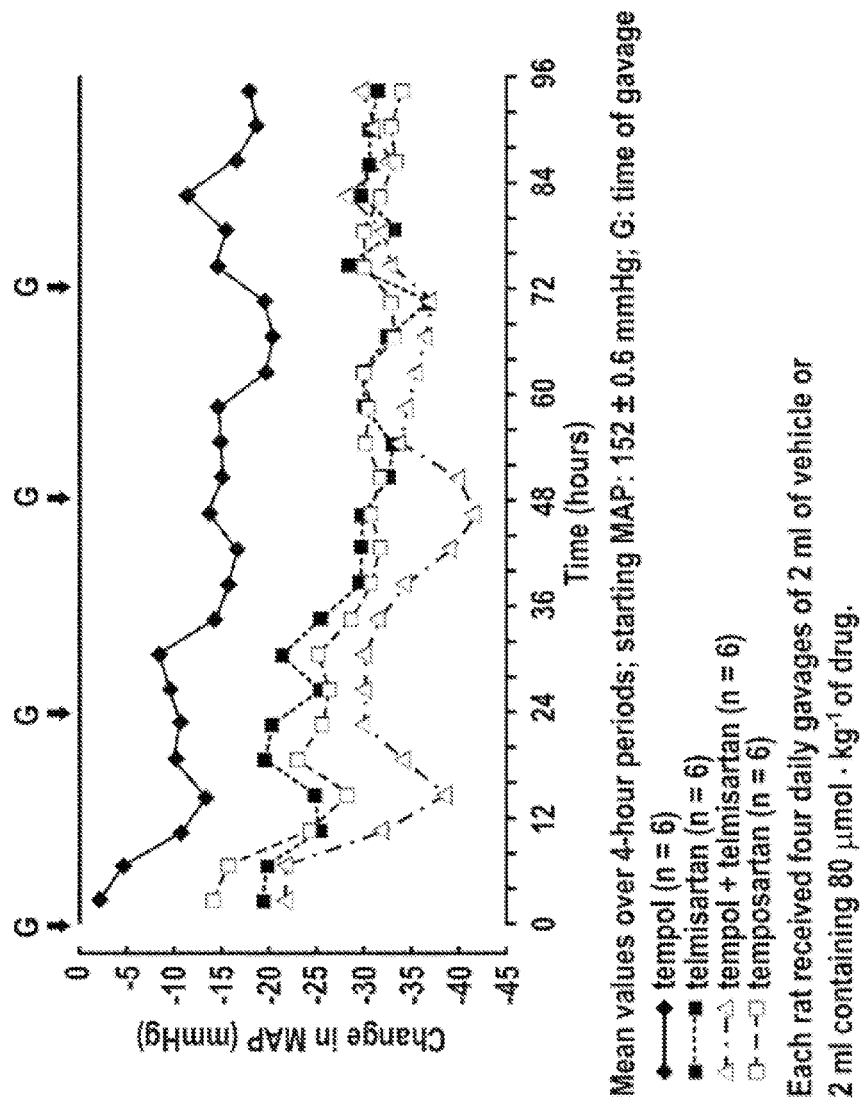

FIG. 6 is a graph depicting mean values (n=6 per group) for vehicle-adjusted changes in MAP after once-daily gavage for four days with 80 mmol kg of the indicated drugs.

Figure 7:
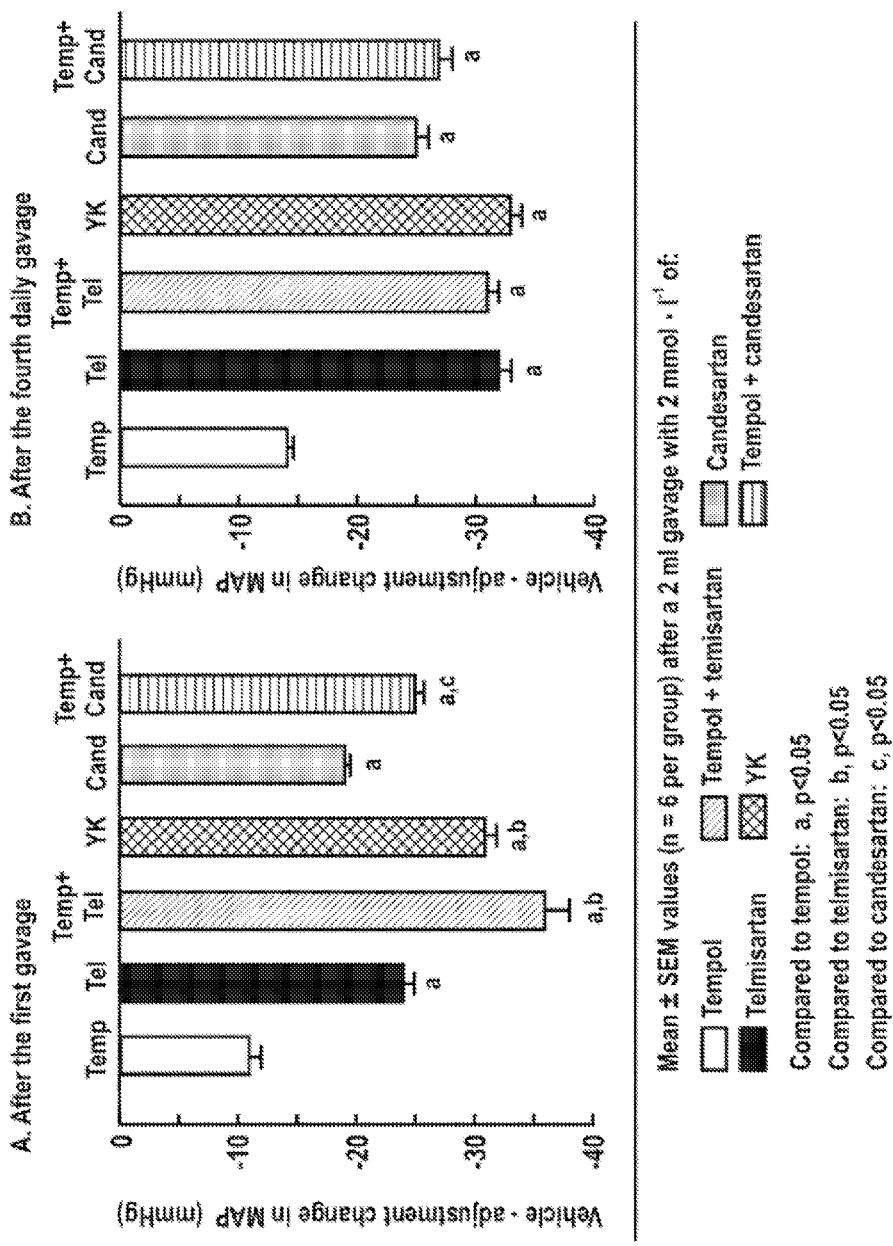

FIG. 7 is a pair of graphs depicting mean±SEM values (n=6) for vehicle-adjusted change in BP 16-24 hours after the first and fourth gavage of the indicated drugs. Temp, tempol; Tel, telmisartan; YK, tempol/telmisartan ester-linked adduct; Cand, candesartan.

FIG. 8 is a table containing MAP and heart rate (HR) of spontaneously hypertensive rats before and after drug administration. Mean±SEM values for conscious spontaneously hypertensive rats gavaged with vehicle or 80 mmol kg at 24 hour intervals with the drugs shown.

DETAILED DESCRIPTION

One aspect of the invention relates to a mixture of tempol and an ARB, such as telmisartan ("tempol+telmisartan"), or a tempol/ARB adduct, such as a tempol/telmisartan ester-linked adduct (YK; "temposartan"), and the use of said mixture or adduct to treat oxidative stress and/or hypertension, by reducing Ang II-stimulated vascular superoxide ($O_2$.$^-$) and blood pressure (BP).

Tempol, which is a redox-cycling nitroxide that acts catalytically to dismutate $O_2$.$^-$ to hydrogen peroxide ($H_2O_2$) (24, 30), was used because effective and validated drugs that reduce $O_2$.$^-$ are not yet available for use in clinical studies (12). Tempol is an antihypertensive agent in many animal models (50) including the spontaneously hypertensive rats (46). It was found that the combination of tempol with an ARB (i.e., telmisartan) either given as two agents together or as a novel, ester-linked compound (tempol/telmisartan ester-linked adduct) is more effective than either compound alone in reducing $O_2$.$^-$ generation in angiotensin II (Ang II)-stimulated preglomerular vascular smooth muscle cells (PGVSMCs) cultured from spontaneously hypertensive rats, and reducing blood pressure in conscious, salt-loaded spontaneously hypertensive rats. Additional studies of BP were undertaken with candesartan in place of telmisartan.

In fact, as described more fully in the Exemplification section, it was found that an ester-linked tempol-telmisartan adduct (YK; temposartan) and a combination of tempol and telmisartan (tempol+telmisartan) both retained the full effect of either drug on AT1-R binding and showed a 100-fold to 1000-fold enhanced sensitivity as a cellular antioxidant in Ang II-stimulated preglomerular vascular smooth muscle cells. Tempol+telmisartan, tempol+candesartan, and tempol/telmisartan ester-linked adduct are all significantly more effective in reducing the BP of conscious spontaneously hypertensive rats 16-24 hours after dosing than either drug alone. This indicates that tempol and ARBs can reduce BP additively and, therefore, can act via independent pathways. However, this additive effect was lost in the salt-loaded SHR model used. This may relate to the unusually angiotensin-dependent hypertension in the SHR which may have biased the results in favor of ARB, relative to the temporal and the adduct in this model.

As noted above, telmisartan combines AT1-R blocking and PPARγ signaling activity. The latter effect could confer additional antiatherogenic (15), anti-inflammatory (53), antioxidant (28) and insulin-sensitizing (52) actions, downregulate AT1-receptor expression (16) and increase adiponectin (52) and nitric oxide activity and endothelial function (35). The maximum reduction in BP in conscious spontaneously hypertensive rats after the first dose of tempol/telmisartan ester-linked adduct, tempol+telmisartan, or tempol+candesartan was significantly greater than either drug individually, but this additive effect was lost over four days of administration. Some of these effects may be a consequence of the upregulation by telmisartan of endothelial cell dimethylarginine dimethylaminohydrolase (DDAH) activity which reduces the accumulation of the endogenous nitric oxide synthase (NOS) inhibitor, asymmetric dimethylarginine (ADMA) (38). This effect was attributed to the PPARγ signaling, and not the AT1-R blocking action of telmisartan (38) since it was not seen with another AT1-R blocking drug, eprosartan. While not intending to be bound by any one mechanism, presumably the predominant effect of telmisartan on BP in this model of Ang II-stimulated cells is via AT1-receptor blockade. Moreover, again not intending to be bound by any one mechanism, the predominant mechanism for interaction between telmisartan and tempol in reducing BP also likely relates to telmisartan's AT1-receptor blocking action since a strictly similar interaction was seen with candesartan and tempol (FIG. 7). Candesartan does not have significant PPARγ agonist activity (6). Therefore, the interaction between tempol and ARBs appears to be a class effect.

Adducts

One aspect of the invention relates to a compound of formula I:

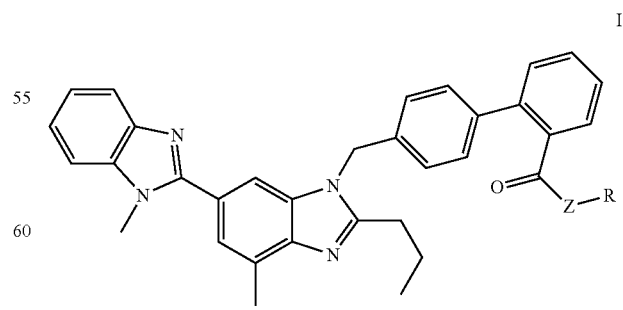

I or a pharmaceutically acceptable salt thereof, wherein, independently for each occurrence, Z is —O—, —N(H)— or —N(alkyl)-; R is

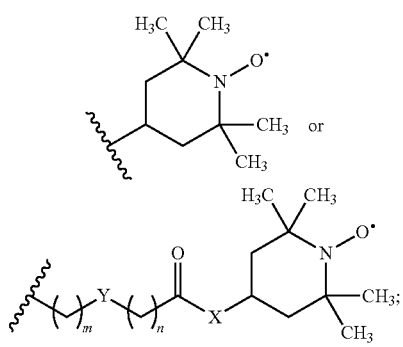

Y is —CH$_2$—, —C(H)═C(H)—, —C≡C—, —C(═O)—, —O—, —N(H)—, —N(alkyl)-, —C(═O)O—, —C(═O)N(H)—, —C(═O)N(alkyl)-, —OC(═O)O—, —N(H)C(═O)—, —N(alkyl)C(═O)—, arylene, or heteroarylene; X is —O—, —CH$_2$—, —N(H)— or —N(alkyl)-; m is 0-10; and n is 0-10; provided the sum of m and n is less than or equal to 10.

In certain embodiments, the present invention relates to any one of the aforementioned compounds, wherein Z is —O—. In certain embodiments, the present invention relates to any one of the aforementioned compounds, wherein Z is —N(H)—. In certain embodiments, the present invention relates to any one of the aforementioned compounds, wherein Z is —N(alkyl)-.

In certain embodiments, the present invention relates to any one of the aforementioned compounds, wherein R is

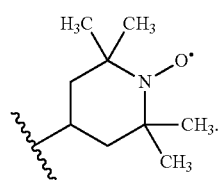

In certain embodiments, the present invention relates to any one of the aforementioned compounds, wherein R is

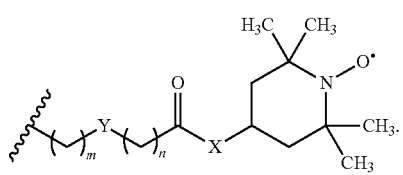

In certain embodiments, the present invention relates to any one of the aforementioned compounds, wherein Y is —CH$_2$—. In certain embodiments, the present invention relates to any one of the aforementioned compounds, wherein Y is —O—. In certain embodiments, the present invention relates to any one of the aforementioned compounds, wherein Y is arylene. In certain embodiments, the present invention relates to any one of the aforementioned compounds, wherein Y is heteroarylene.

In certain embodiments, the present invention relates to any one of the aforementioned compounds, wherein X is —CH$_2$—. In certain embodiments, the present invention relates to any one of the aforementioned compounds, wherein X is —O—. In certain embodiments, the present invention relates to any one of the aforementioned compounds, wherein X is —N(H)—. In certain embodiments, the present invention relates to any one of the aforementioned compounds, wherein X is —N(alkyl)-.

In certain embodiments, the present invention relates to any one of the aforementioned compounds, wherein m is 0. In certain embodiments, the present invention relates to any one of the aforementioned compounds, wherein m is 1. In certain embodiments, the present invention relates to any one of the aforementioned compounds, wherein m is 2. In certain embodiments, the present invention relates to any one of the aforementioned compounds, wherein m is 3. In certain embodiments, the present invention relates to any one of the aforementioned compounds, wherein m is 4. In certain embodiments, the present invention relates to any one of the aforementioned compounds, wherein m is 5. In certain embodiments, the present invention relates to any one of the aforementioned compounds, wherein m is 6. In certain embodiments, the present invention relates to any one of the aforementioned compounds, wherein m is 7. In certain embodiments, the present invention relates to any one of the aforementioned compounds, wherein m is 8. In certain embodiments, the present invention relates to any one of the aforementioned compounds, wherein m is 9. In certain embodiments, the present invention relates to any one of the aforementioned compounds, wherein m is 10.

In certain embodiments, the present invention relates to any one of the aforementioned compounds, wherein n is 0. In certain embodiments, the present invention relates to any one of the aforementioned compounds, wherein n is 1. In certain embodiments, the present invention relates to any one of the aforementioned compounds, wherein n is 2. In certain embodiments, the present invention relates to any one of the aforementioned compounds, wherein n is 3. In certain embodiments, the present invention relates to any one of the aforementioned compounds, wherein n is 4. In certain embodiments, the present invention relates to any one of the aforementioned compounds, wherein n is 5. In certain embodiments, the present invention relates to any one of the aforementioned compounds, wherein n is 6. In certain embodiments, the present invention relates to any one of the aforementioned compounds, wherein n is 7. In certain embodiments, the present invention relates to any one of the aforementioned compounds, wherein n is 8. In certain embodiments, the present invention relates to any one of the aforementioned compounds, wherein n is 9. In certain embodiments, the present invention relates to any one of the aforementioned compounds, wherein n is 10.

In certain embodiments, the present invention relates to any one of the aforementioned compounds, wherein m is 0 and n is 0.

In certain embodiments, the present invention relates to any one of the aforementioned compounds, wherein Z is —O—; m is 0; and n is 0.

In one embodiment, the present invention relates to a compound of Formula I wherein Z is —O—; and R is

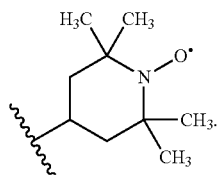

In one embodiment, the present invention relates to a compound of Formula I wherein Z is —N(H)—; and R is

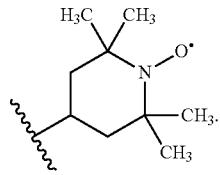

One aspect of the invention relates to a compound of formula II:

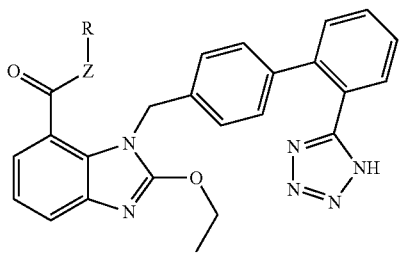

or a pharmaceutically acceptable salt thereof, wherein, independently for each occurrence, Z is —O—, —N(H)— or —N(alkyl)-; R is

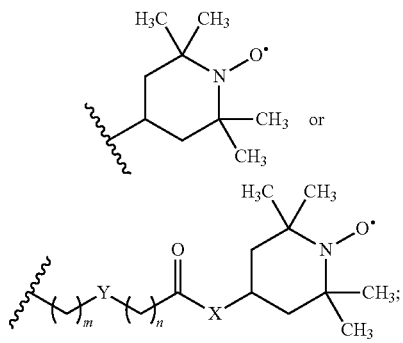

Y is —CH$_2$—, —C(H)=C(H)—, —C≡C—, —C(=O)—, —O—, —N(H)—, —N(alkyl)-, —C(=O)O—, —C(=O)N(H)—, —C(=O)N(alkyl)-, —OC(=O)O—, —N(H)C(=O)—, —N(alkyl)C(=O)—, arylene, or heteroarylene; m is 0-10; X is —O—, —CH$_2$—, —N(H)— or —N(alkyl)-; and n is 0-10; provided the sum of m and n is less than or equal to 10.

In certain embodiments, the present invention relates to any one of the aforementioned compounds, wherein Z is —O—. In certain embodiments, the present invention relates to any one of the aforementioned compounds, wherein Z is —N(H)—. In certain embodiments, the present invention relates to any one of the aforementioned compounds, wherein Z is —N(alkyl)-.

In certain embodiments, the present invention relates to any one of the aforementioned compounds, wherein R is

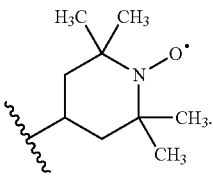

In certain embodiments, the present invention relates to any one of the aforementioned compounds, wherein R is

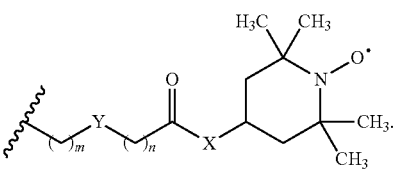

In certain embodiments, the present invention relates to any one of the aforementioned compounds, wherein Y is —CH$_2$—. In certain embodiments, the present invention relates to any one of the aforementioned compounds, wherein Y is —O—. In certain embodiments, the present invention relates to any one of the aforementioned compounds, wherein Y is arylene. In certain embodiments, the present invention relates to any one of the aforementioned compounds, wherein Y is heteroarylene.

In certain embodiments, the present invention relates to any one of the aforementioned compounds, wherein X is —CH$_2$—. In certain embodiments, the present invention relates to any one of the aforementioned compounds, wherein X is —O—. In certain embodiments, the present invention relates to any one of the aforementioned compounds, wherein X is —N(H)—. In certain embodiments, the present invention relates to any one of the aforementioned compounds, wherein X is —N(alkyl)-.

In certain embodiments, the present invention relates to any one of the aforementioned compounds, wherein m is 0. In certain embodiments, the present invention relates to any one of the aforementioned compounds, wherein m is 1. In certain embodiments, the present invention relates to any one of the aforementioned compounds, wherein m is 2. In certain embodiments, the present invention relates to any one of the aforementioned compounds, wherein m is 3. In certain embodiments, the present invention relates to any one of the aforementioned compounds, wherein m is 4. In certain embodiments, the present invention relates to any one of the aforementioned compounds, wherein m is 5. In certain embodiments, the present invention relates to any one of the aforementioned compounds, wherein m is 6. In certain embodiments, the present invention relates to any one of the aforementioned compounds, wherein m is 7. In certain embodiments, the present invention relates to any one of the aforementioned compounds, wherein m is 8. In certain embodiments, the present invention relates to any one of the aforementioned compounds, wherein m is 9. In certain embodiments, the present invention relates to any one of the aforementioned compounds, wherein m is 10.

In certain embodiments, the present invention relates to any one of the aforementioned compounds, wherein n is 0. In certain embodiments, the present invention relates to any one of the aforementioned compounds, wherein n is 1. In certain embodiments, the present invention relates to any one of the aforementioned compounds, wherein n is 2. In certain embodiments, the present invention relates to any one of the aforementioned compounds, wherein n is 3. In certain embodiments, the present invention relates to any one of the aforementioned compounds, wherein n is 4. In certain embodiments, the present invention relates to any one of the aforementioned compounds, wherein n is 5. In certain embodiments, the present invention relates to any one of the aforementioned compounds, wherein n is 6. In certain embodiments, the present invention relates to any one of the aforementioned compounds, wherein n is 7. In certain embodiments, the present invention relates to any one of the aforementioned compounds, wherein n is 8. In certain embodiments, the present invention relates to any one of the aforementioned compounds, wherein n is 9. In certain embodiments, the present invention relates to any one of the aforementioned compounds, wherein n is 10.

In certain embodiments, the present invention relates to any one of the aforementioned compounds, wherein m is 0 and n is 0.

In certain embodiments, the present invention relates to any one of the aforementioned compounds, wherein Z is —O—; m is 0; and n is 0.

Pharmaceutical Compositions

One or more mixtures (e.g., tempol+telmisartan or tempol+candesartan) or compounds (e.g., tempol/telmisartan ester-linked adduct) of this invention can be administered to a subject by themselves or in pharmaceutical compositions where they are mixed with biologically suitable carriers or excipient(s) at doses to treat or ameliorate a disease or condition as described herein. For example, one aspect of the invention relates to pharmaceutical composition comprising a therapeutically effective dose of a tempol and ARB, or an adduct thereof, and a pharmaceutically acceptable diluent or carrier. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, ocular, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, administration may be in a local rather than a systemic manner, for example, via injection of a compound directly into a specific anatomical site, often in a depot or sustained release formulation.

Furthermore, the administration may be in a targeted drug delivery system, for example, in a liposome coated with cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the mixtures or adducts of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the mixtures or adducts can be formulated readily by combining the active compounds with pharmaceutically acceptable carriers well known in the art. Such carriers enable the mixtures or adducts of the invention to be formulated as tablets, pills, dragees, capsules, liquids, gels, syrups, slurries, suspensions and the like, for oral ingestion by a subject to be treated. Pharmaceutical preparations for oral use can be obtained by combining the mixtures or adducts of the invention with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

In one embodiment the pharmaceutically acceptable carrier excludes dimethylsulfoxide (DMSO).

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the mixtures or adducts for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The mixtures or adducts of the invention can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the mixtures or adducts of the invention may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the mixtures or adducts of the invention may be in powder form for constitution with a suitable vehicle, e.g., sterile pyrogen-free water, before use.

The mixtures or adducts of the invention may also be formulated in rectal compositions such as suppositories or retention enemas, e.g., containing conventional suppository bases such as cocoa butter or other glycerides.

In addition to the formulations described previously, the mixtures or adducts of the invention may also be formulated as a depot preparation. Such long acting formulations may be administered by implantation (for example subcutaneously or intramuscularly or by intramuscular injection). Thus, for example, the mixtures or adducts of the invention may be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide (DMSO) also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, .beta.-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di alkyl-N-(hydroxy alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Pharmaceutical compositions suitable for use in the present invention include compositions wherein the active ingredients in the mixtures, or the adducts, are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

The combination therapy contemplated by the invention includes, for example, administration of a compound of the invention, or a pharmaceutically acceptable salt thereof, and additional agent(s) in a single pharmaceutical formulation (described as a mixture herein) as well as administration of a compound of the invention, or a pharmaceutically acceptable salt thereof, and additional agent(s) in separate pharmaceutical formulations. In other words, co-administration shall mean the administration of at least two agents to a subject so as to provide the beneficial effects of the combination of both agents. For example, the agents may be administered essentially simultaneously or sequentially over a period of time.

One aspect of the invention relates to a pharmaceutical composition comprising tempol, an angiotensin receptor blocker, and a pharmaceutically acceptable carrier. Another aspect of the invention relates to a pharmaceutical composition consisting essentially of tempol, an angiotensin receptor blocker, and a pharmaceutically acceptable carrier. Another aspect of the invention relates to a pharmaceutical composition consisting of tempol, an angiotensin receptor blocker, and a pharmaceutically acceptable carrier. In one embodiment, the pharmaceutically acceptable carrier excludes dimethylsulfoxide (DMSO).

In certain embodiments, the present invention relates to any one of the aforementioned pharmaceutical compositions, wherein said angiotensin receptor blocker is telmisartan. In certain embodiments, the present invention relates to any one of the aforementioned pharmaceutical compositions, wherein said angiotensin receptor blocker is candesartan.

One aspect of the invention relates to a pharmaceutical composition comprising an adduct of tempol and an angiotensin receptor blocker, and a pharmaceutically acceptable carrier. Another aspect of the invention relates to a pharmaceutical composition consisting essentially of an adduct of tempol and an angiotensin receptor blocker, and a pharmaceutically acceptable carrier. Another aspect of the invention relates to a pharmaceutical composition consisting of an adduct of tempol and an angiotensin receptor blocker, and a pharmaceutically acceptable carrier. In one embodiment, the pharmaceutically acceptable carrier excludes dimethylsulfoxide (DMSO).

In certain embodiments, the present invention relates to any one of the aforementioned pharmaceutical compositions, wherein said adduct is a compound of formula I:

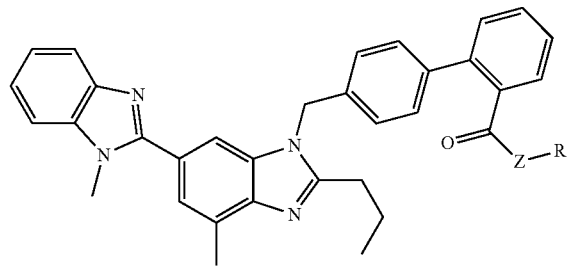

I or a pharmaceutically acceptable salt thereof, wherein, independently for each occurrence, Z is —O—, —N(H)— or —N(alkyl)-; R is

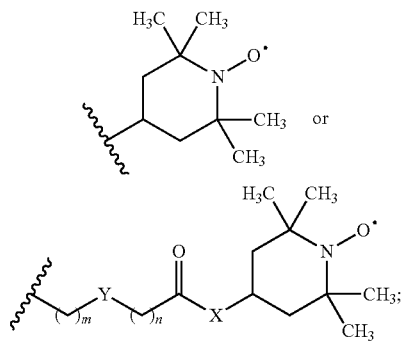

Y is —CH$_2$—, —C(H)=C(H)—, —C≡C—, —C(=O)—, —O—, —N(H)—, —N(alkyl)-, —C(=O)O—, —C(=O)N(H)—, —C(=O)N(alkyl)-, —OC(=O)O—, —N(H)C(=O)—, —N(alkyl)C(=O)—, arylene, or heteroarylene; m is 0-10; X is —O—, —CH$_2$—, —N(H)— or —N(alkyl)-; and n is 0-10; provided the sum of m and n is less than or equal to 10.

In certain embodiments, the present invention relates to any one of the aforementioned pharmaceutical compositions, wherein Z is —O—. In certain embodiments, the present invention relates to any one of the aforementioned pharmaceutical compositions, wherein Z is —N(H)—. In certain embodiments, the present invention relates to any one of the aforementioned pharmaceutical compositions, wherein Z is —N(alkyl)-.

In certain embodiments, the present invention relates to any one of the aforementioned pharmaceutical compositions, wherein R is

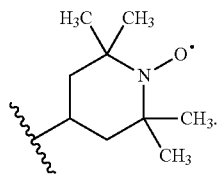

In certain embodiments, the present invention relates to any one of the aforementioned pharmaceutical compositions, wherein R is

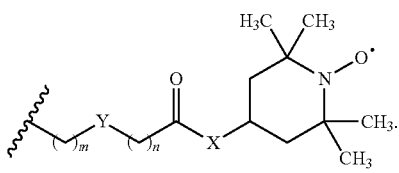

In certain embodiments, the present invention relates to any one of the aforementioned pharmaceutical compositions, wherein Y is —CH$_2$—. In certain embodiments, the present invention relates to any one of the aforementioned pharmaceutical compositions, wherein Y is —O—. In certain embodiments, the present invention relates to any one of the aforementioned pharmaceutical compositions, wherein Y is arylene. In certain embodiments, the present invention relates to any one of the aforementioned pharmaceutical compositions, wherein Y is heteroarylene.

In certain embodiments, the present invention relates to any one of the aforementioned pharmaceutical compositions, wherein X is —CH$_2$—. In certain embodiments, the present invention relates to any one of the aforementioned pharmaceutical compositions, wherein X is —O—. In certain embodiments, the present invention relates to any one of the aforementioned pharmaceutical compositions, wherein X is —N(H)—. In certain embodiments, the present invention relates to any one of the aforementioned pharmaceutical compositions, wherein X is —N(alkyl)-.

In certain embodiments, the present invention relates to any one of the aforementioned pharmaceutical compositions, wherein m is 0. In certain embodiments, the present invention relates to any one of the aforementioned pharmaceutical compositions, wherein m is 1. In certain embodiments, the present invention relates to any one of the aforementioned pharmaceutical compositions, wherein m is 2. In certain embodiments, the present invention relates to any one of the aforementioned pharmaceutical compositions, wherein m is 3. In certain embodiments, the present invention relates to any one of the aforementioned pharmaceutical compositions, wherein m is 4. In certain embodiments, the present invention relates to any one of the aforementioned pharmaceutical compositions, wherein m is 5. In certain embodiments, the present invention relates to any one of the aforementioned pharmaceutical compositions, wherein m is 6. In certain embodiments, the present invention relates to any one of the aforementioned pharmaceutical compositions, wherein m is 7. In certain embodiments, the present invention relates to any one of the aforementioned pharmaceutical compositions, wherein m is 8. In certain embodiments, the present invention relates to any one of the aforementioned pharmaceutical compositions, wherein m is 9. In certain embodiments, the present invention relates to any one of the aforementioned pharmaceutical compositions, wherein m is 10.

In certain embodiments, the present invention relates to any one of the aforementioned pharmaceutical compositions, wherein n is 0. In certain embodiments, the present invention relates to any one of the aforementioned pharmaceutical compositions, wherein n is 1. In certain embodiments, the present invention relates to any one of the aforementioned pharmaceutical compositions, wherein n is 2. In certain embodiments, the present invention relates to any one of the aforementioned pharmaceutical compositions, wherein n is 3. In certain embodiments, the present invention relates to any one of the aforementioned pharmaceutical compositions, wherein n is 4. In certain embodiments, the present invention relates to any one of the aforementioned pharmaceutical compositions, wherein n is 5. In certain embodiments, the present invention relates to any one of the aforementioned pharmaceutical compositions, wherein n is 6. In certain embodiments, the present invention relates to any one of the aforementioned pharmaceutical compositions, wherein n is 7. In certain embodiments, the present invention relates to any one of the aforementioned pharmaceutical compositions, wherein n is 8. In certain embodiments, the present invention relates to any one of the aforementioned pharmaceutical compositions, wherein n is 9. In certain embodiments, the present invention relates to any one of the aforementioned pharmaceutical compositions, wherein n is 10.

In certain embodiments, the present invention relates to any one of the aforementioned pharmaceutical compositions, wherein m is 0 and n is 0.

In certain embodiments, the present invention relates to any one of the aforementioned pharmaceutical compositions, wherein Z is —O—; m is 0; and n is 0.

In certain embodiments, the present invention relates to any one of the aforementioned pharmaceutical compositions, wherein said adduct is a compound of formula II:

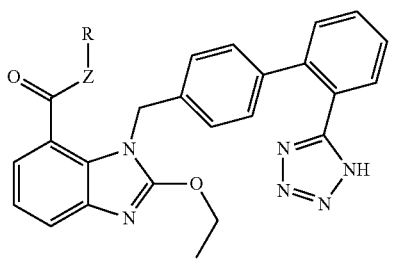

II or a pharmaceutically acceptable salt thereof, wherein, independently for each occurrence, Z is —O—, —N(H)— or —N(alkyl)-; R is

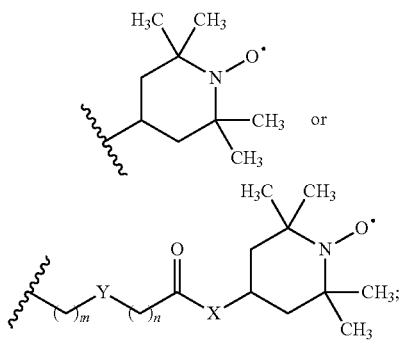

Y is —CH$_2$—, —C(H)=C(H)—, —C≡C—, —C(=O)—, —O—, —N(H)—, —N(alkyl)-, —C(=O)O—, —C(=O)N(H)—, —C(=O)N(alkyl)-, —OC(=O)O—, —N(H)C(=O)—, —N(alkyl)C(=O)—, arylene, or heteroarylene; m is 0-10; X is —O—, —CH$_2$—, —N(H)— or —N(alkyl)-; and n is 0-10; provided the sum of m and n is less than or equal to 10.

In certain embodiments, the present invention relates to any one of the aforementioned pharmaceutical compositions, wherein Z is —O—. In certain embodiments, the present invention relates to any one of the aforementioned pharmaceutical compositions, wherein Z is —N(H)—. In certain embodiments, the present invention relates to any one of the aforementioned pharmaceutical compositions, wherein Z is —N(alkyl)-.

In certain embodiments, the present invention relates to any one of the aforementioned pharmaceutical compositions, wherein R is

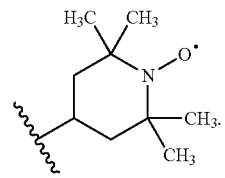

In certain embodiments, the present invention relates to any one of the aforementioned pharmaceutical compositions, wherein R is

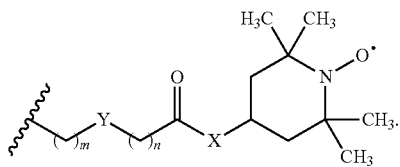

In certain embodiments, the present invention relates to any one of the aforementioned pharmaceutical compositions, wherein Y is —CH$_2$—. In certain embodiments, the present invention relates to any one of the aforementioned pharmaceutical compositions, wherein Y is —O—. In certain embodiments, the present invention relates to any one of the aforementioned pharmaceutical compositions, wherein Y is arylene. In certain embodiments, the present invention relates to any one of the aforementioned pharmaceutical compositions, wherein Y is heteroarylene.

In certain embodiments, the present invention relates to any one of the aforementioned pharmaceutical compositions, wherein X is —$CH_2$—. In certain embodiments, the present invention relates to any one of the aforementioned pharmaceutical compositions, wherein X is —O—. In certain embodiments, the present invention relates to any one of the aforementioned pharmaceutical compositions, wherein X is —N(H)—. In certain embodiments, the present invention relates to any one of the aforementioned pharmaceutical compositions, wherein X is —N(alkyl)-.

In certain embodiments, the present invention relates to any one of the aforementioned pharmaceutical compositions, wherein m is 0. In certain embodiments, the present invention relates to any one of the aforementioned pharmaceutical compositions, wherein m is 1. In certain embodiments, the present invention relates to any one of the aforementioned pharmaceutical compositions, wherein m is 2. In certain embodiments, the present invention relates to any one of the aforementioned pharmaceutical compositions, wherein m is 3. In certain embodiments, the present invention relates to any one of the aforementioned pharmaceutical compositions, wherein m is 4. In certain embodiments, the present invention relates to any one of the aforementioned pharmaceutical compositions, wherein m is 5. In certain embodiments, the present invention relates to any one of the aforementioned pharmaceutical compositions, wherein m is 6. In certain embodiments, the present invention relates to any one of the aforementioned pharmaceutical compositions, wherein m is 7. In certain embodiments, the present invention relates to any one of the aforementioned pharmaceutical compositions, wherein m is 8. In certain embodiments, the present invention relates to any one of the aforementioned pharmaceutical compositions, wherein m is 9. In certain embodiments, the present invention relates to any one of the aforementioned pharmaceutical compositions, wherein m is 10.

In certain embodiments, the present invention relates to any one of the aforementioned pharmaceutical compositions, wherein n is 0. In certain embodiments, the present invention relates to any one of the aforementioned pharmaceutical compositions, wherein n is 1. In certain embodiments, the present invention relates to any one of the aforementioned pharmaceutical compositions, wherein n is 2. In certain embodiments, the present invention relates to any one of the aforementioned pharmaceutical compositions, wherein n is 3. In certain embodiments, the present invention relates to any one of the aforementioned pharmaceutical compositions, wherein n is 4. In certain embodiments, the present invention relates to any one of the aforementioned pharmaceutical compositions, wherein n is 5. In certain embodiments, the present invention relates to any one of the aforementioned pharmaceutical compositions, wherein n is 6. In certain embodiments, the present invention relates to any one of the aforementioned pharmaceutical compositions, wherein n is 7. In certain embodiments, the present invention relates to any one of the aforementioned pharmaceutical compositions, wherein n is 8. In certain embodiments, the present invention relates to any one of the aforementioned pharmaceutical compositions, wherein n is 9. In certain embodiments, the present invention relates to any one of the aforementioned pharmaceutical compositions, wherein n is 10.

In certain embodiments, the present invention relates to any one of the aforementioned pharmaceutical compositions, wherein m is 0 and n is 0.

In certain embodiments, the present invention relates to any one of the aforementioned pharmaceutical compositions, wherein Z is —O—; m is 0; and n is 0.

Methods

One aspect the invention provides a method for oxidative stress and/or hypertension in a subject for whom such treatment is beneficial. Uses of this invention include, but are not limited to: prevention and treatment of high blood pressure and its consequences. High blood pressure occurs either alone (essential hypertension), or as a complication of a number of other conditions. Therefore, uses for the invention include hypertension and hypertension associated with heart failure, chronic kidney disease, peripheral vascular disease, stroke, diabetes mellitus, old age, and metabolic syndrome.

The term "treating" as used herein encompasses the administration and/or application of one or more compounds described herein, to a subject, for the purpose of providing prevention of or management of, and/or remedy for a condition. "Treatment" for the purposes of this disclosure, may, but does not have to, provide a cure; rather, "treatment" may be in the form of management of the condition.

The term "preventing" as used herein includes either preventing or slowing the onset of oxidative stress and/or hypertension altogether or preventing or slowing the onset of oxidative stress and/or hypertension in individuals at risk.

The term "subject" for purposes of treatment includes any human or animal subject who has been diagnosed with, has symptoms of, or is at risk of oxidative stress and/or hypertension, or is at risk of developing oxidative stress and/or hypertension on their own, or as a complication of another condition, for example heart failure, diabetes or kidney disease. For methods of prevention, the subject is any human or animal subject. To illustrate, for purposes of prevention, a subject may be a human subject who is at risk of or is genetically predisposed to hypertension or is suffering from heart failure, including both systolic and diastolic heart failure. Besides being useful for human treatment, the compounds described herein are also useful for veterinary treatment of mammals, including companion animals and farm animals, such as, but not limited to, dogs, cats, horses, cows, sheep, and pigs.

A "therapeutically effective amount" is an amount of a compound of the invention or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

One aspect of the invention relates to a method of treating oxidative stress and/or hypertension in a subject comprising the step of co-administering a therapeutically effective amount of both tempol and an angiotensin receptor blocker to said subject.

In certain embodiments, the present invention relates to any one of the aforementioned methods, wherein said tempol and said angiotensin receptor blocker are administered essentially simultaneously.

In certain embodiments, the present invention relates to any one of the aforementioned methods, wherein said tempol and said angiotensin receptor blocker are administered sequentially. The order of administration can be either order, i.e., tempol first, followed by ARB, or ARB first, followed by tempol.

In certain embodiments, the present invention relates to any one of the aforementioned methods, wherein said angiotensin receptor blocker is telmisartan. In certain embodiments, the present invention relates to any one of the aforementioned methods, wherein said angiotensin receptor blocker is candesartan.

In certain embodiments, the present invention relates to any one of the aforementioned methods, wherein said subject is suffering from diastolic heart failure.

Another aspect of the invention relates to a method of treating oxidative stress and/or hypertension in a subject comprising the step of administering a therapeutically effective amount of a tempol-angiotensin receptor blocker adduct to said subject.

In certain embodiments, the present invention relates to any one of the aforementioned methods, wherein said subject is suffering from diastolic heart failure.

In certain embodiments, the present invention relates to any one of the aforementioned methods, wherein said adduct is a compound of formula I:

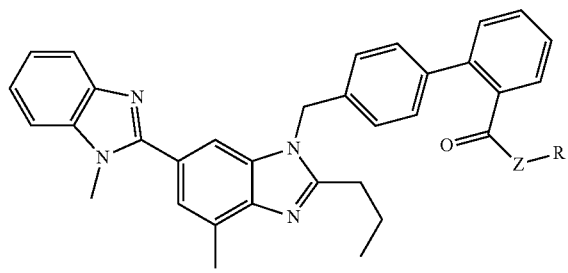

I or a pharmaceutically acceptable salt thereof, wherein, independently for each occurrence, Z is —O—, —N(H)— or —N(alkyl)-; R is

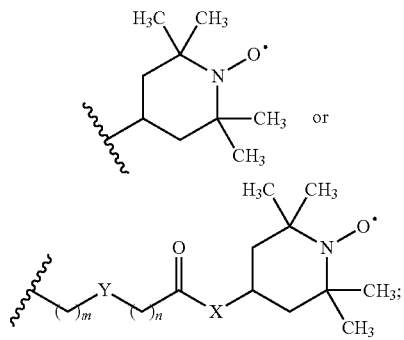

Y is —CH$_2$—, —C(H)=C(H)—, —C≡C—, —C(=O)—, —O—, —N(H)—, —N(alkyl)-, —C(=O)O—, —C(=O)N(H)—, —C(=O)N(alkyl)-, —OC(=O)O—, —N(H)C(=O)—, —N(alkyl)C(=O)—, arylene, or heteroarylene; m is 0-10; X is —O—, —CH$_2$—, —N(H)— or —N(alkyl)-; and n is 0-10; provided the sum of m and n is less than or equal to 10.

In certain embodiments, the present invention relates to any one of the aforementioned methods, wherein Z is —O—. In certain embodiments, the present invention relates to any one of the aforementioned methods, wherein Z is —N(H)—. In certain embodiments, the present invention relates to any one of the aforementioned methods, wherein Z is —N(alkyl)-.

In certain embodiments, the present invention relates to any one of the aforementioned methods, wherein R is

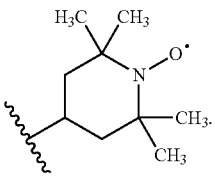

In certain embodiments, the present invention relates to any one of the aforementioned methods, wherein R is

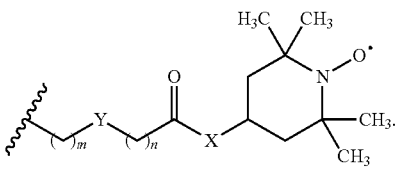

In certain embodiments, the present invention relates to any one of the aforementioned methods, wherein Y is —CH$_2$—. In certain embodiments, the present invention relates to any one of the aforementioned methods, wherein Y is —O—. In certain embodiments, the present invention relates to any one of the aforementioned methods, wherein Y is arylene. In certain embodiments, the present invention relates to any one of the aforementioned methods, wherein Y is heteroarylene.

In certain embodiments, the present invention relates to any one of the aforementioned methods, wherein X is —CH$_2$—. In certain embodiments, the present invention relates to any one of the aforementioned methods, wherein X is —O—. In certain embodiments, the present invention relates to any one of the aforementioned methods, wherein X is —N(H)—. In certain embodiments, the present invention relates to any one of the aforementioned methods, wherein X is —N(alkyl)-.

In certain embodiments, the present invention relates to any one of the aforementioned methods, wherein m is 0. In certain embodiments, the present invention relates to any one of the aforementioned methods, wherein m is 1. In certain embodiments, the present invention relates to any one of the aforementioned methods, wherein m is 2. In certain embodiments, the present invention relates to any one of the aforementioned methods, wherein m is 3. In certain embodiments, the present invention relates to any one of the aforementioned methods, wherein m is 4. In certain embodiments, the present invention relates to any one of the aforementioned methods, wherein m is 5. In certain embodiments, the present invention relates to any one of the aforementioned methods, wherein m is 6. In certain embodiments, the present invention relates to any one of the aforementioned methods, wherein m is 7. In certain embodiments, the present invention relates to any one of the aforementioned methods, wherein m is 8. In certain embodiments, the present invention relates to any one of the aforementioned methods, wherein m is 9. In certain embodiments, the present invention relates to any one of the aforementioned methods, wherein m is 10.

In certain embodiments, the present invention relates to any one of the aforementioned methods, wherein n is 0. In certain embodiments, the present invention relates to any one of the aforementioned methods, wherein n is 1. In certain embodiments, the present invention relates to any one of the aforementioned methods, wherein n is 2. In certain embodiments, the present invention relates to any one of the aforementioned methods, wherein n is 3. In certain embodiments, the present invention relates to any one of the aforementioned methods, wherein n is 4. In certain embodiments, the present invention relates to any one of the aforementioned methods, wherein n is 5. In certain embodiments, the present invention relates to any one of the aforementioned methods, wherein n is 6. In certain embodiments, the present invention relates to any one of the aforementioned methods, wherein n is 7. In certain embodiments, the present invention relates to any one of the aforementioned methods, wherein n is 8. In certain embodiments, the present invention relates to any one of the aforementioned methods, wherein n is 9. In certain embodiments, the present invention relates to any one of the aforementioned methods, wherein n is 10.

In certain embodiments, the present invention relates to any one of the aforementioned methods, wherein m is 0 and n is 0.

In certain embodiments, the present invention relates to any one of the aforementioned methods, wherein Z is —O—; m is 0; and n is 0.

In certain embodiments, the present invention relates to any one of the aforementioned methods, wherein said adduct is a compound of formula II:

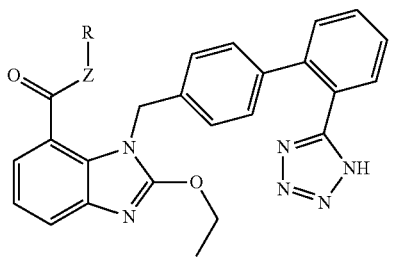

or a pharmaceutically acceptable salt thereof, wherein, independently for each occurrence, Z is —O—, —N(H)— or —N(alkyl)-; R is

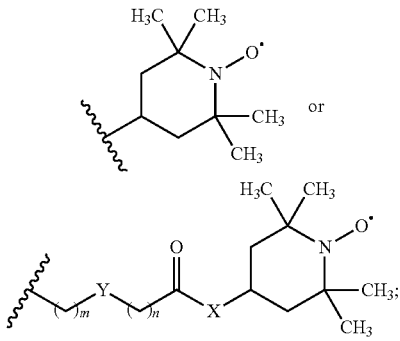

Y is —CH$_2$—, —C(H)=C(H)—, —C≡C—, —C(=O)—, —O—, —N(H)—, —N(alkyl)-, —C(=O)O—, —C(=O)N(H)—, —C(=O)N(alkyl)-, —OC(=O)O—, —N(H)C(=O)—, —N(alkyl)C(=O)—, arylene, or heteroarylene; m is 0-10; X is —O—, —CH$_2$—, —N(H)— or —N(alkyl)-; and n is 0-10; provided the sum of m and n is less than or equal to 10.

In certain embodiments, the present invention relates to any one of the aforementioned methods, wherein Z is —O—. In certain embodiments, the present invention relates to any one of the aforementioned methods, wherein Z is —N(H)—.

In certain embodiments, the present invention relates to any one of the aforementioned methods, wherein Z is —N(alkyl)-.

In certain embodiments, the present invention relates to any one of the aforementioned methods, wherein R is

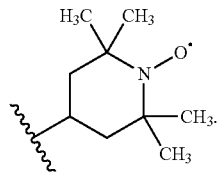

In certain embodiments, the present invention relates to any one of the aforementioned methods, wherein R is

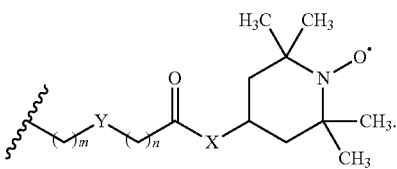

In certain embodiments, the present invention relates to any one of the aforementioned methods, wherein Y is —CH$_2$—. In certain embodiments, the present invention relates to any one of the aforementioned methods, wherein Y is —O—. In certain embodiments, the present invention relates to any one of the aforementioned methods, wherein Y is arylene. In certain embodiments, the present invention relates to any one of the aforementioned methods, wherein Y is heteroarylene.

In certain embodiments, the present invention relates to any one of the aforementioned methods, wherein X is —CH$_2$—. In certain embodiments, the present invention relates to any one of the aforementioned methods, wherein X is —O—. In certain embodiments, the present invention relates to any one of the aforementioned methods, wherein X is —N(H)—. In certain embodiments, the present invention relates to any one of the aforementioned methods, wherein X is —N(alkyl)-.

In certain embodiments, the present invention relates to any one of the aforementioned methods, wherein m is 0. In certain embodiments, the present invention relates to any one of the aforementioned methods, wherein m is 1. In certain embodiments, the present invention relates to any one of the aforementioned methods, wherein m is 2. In certain embodiments, the present invention relates to any one of the aforementioned methods, wherein m is 3. In certain embodiments, the present invention relates to any one of the aforementioned methods, wherein m is 4. In certain embodiments, the present invention relates to any one of the aforementioned methods, wherein m is 5. In certain embodiments, the present invention relates to any one of the aforementioned methods, wherein m is 6. In certain embodiments, the present invention relates to any one of the aforementioned methods, wherein m is 7. In certain embodiments, the present invention relates to any one of the aforementioned methods, wherein m is 8. In certain embodiments, the present invention relates to any one of the aforementioned methods, wherein m is 9. In certain embodiments, the present invention relates to any one of the aforementioned methods, wherein m is 10.

In certain embodiments, the present invention relates to any one of the aforementioned methods, wherein n is 0. In certain embodiments, the present invention relates to any one of the aforementioned methods, wherein n is 1. In certain embodiments, the present invention relates to any one of the aforementioned methods, wherein n is 2. In certain embodiments, the present invention relates to any one of the aforementioned methods, wherein n is 3. In certain embodiments, the present invention relates to any one of the aforementioned methods, wherein n is 4. In certain embodiments, the present invention relates to any one of the aforementioned methods, wherein n is 5. In certain embodiments, the present invention relates to any one of the aforementioned methods, wherein n is 6. In certain embodiments, the present invention relates to any one of the aforementioned methods, wherein n is 7. In certain embodiments, the present invention relates to any one of the aforementioned methods, wherein n is 8. In certain embodiments, the present invention relates to any one of the aforementioned methods, wherein n is 9. In certain embodiments, the present invention relates to any one of the aforementioned methods, wherein n is 10.

In certain embodiments, the present invention relates to any one of the aforementioned methods, wherein m is 0 and n is 0.

In certain embodiments, the present invention relates to any one of the aforementioned methods, wherein Z is —O—; m is 0; and n is 0.

Another aspect of the invention relates to the use of the compounds of the invention for imaging (in vitro and in vivo) by magnetic resonance, electron paramagnetic resonance (EPR) and/or electron spin resonance (ESR) spectroscopy.

DEFINITIONS

All definitions, as defined and used herein, should be understood to control over dictionary definitions, definitions in documents incorporated by reference, and/or ordinary meanings of the defined terms.

For purposes of this invention, the chemical elements are identified in accordance with the Periodic Table of the Elements, CAS version, Handbook of Chemistry and Physics, 67th Ed., 1986-87, inside cover.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein "angiotensin receptor blocker" (ARB) refer to a compound that blocks the action of angiotensin II. Currently commercially available ARBs include telmisartan, candesartan, losartan, irbesartan, valsartan and eprosartan.

As used herein "telmisartan" refers to a compound with the following structure

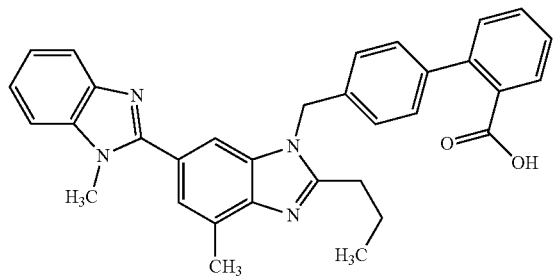 [SMILES: CCCc1nc2c(C)cc(-c3nc4ccccc4n3C)cc2n1Cc1ccc(-c2ccccc2C(=O)O)cc1]

or a pharmaceutically acceptable salt thereof. An adduct of telmisartan refers to telmisartan covalently bound to another molecule through its carboxylic acid (e.g., via an ester or amide bond).

As used herein "candesartan" refers to a compound with the following structure

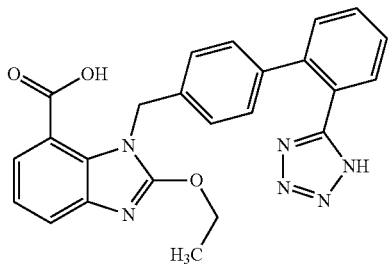 [SMILES: CCOc1nc2cccc(C(=O)O)c2n1Cc1ccc(-c2ccccc2-c2nnn[nH]2)cc1]

or a pharmaceutically acceptable salt thereof. An adduct of candesartan refers to candesartan covalently bound to another molecule through its carboxylic acid (e.g., via an ester or amide bond).

As used herein "tempol" refers to a compound with the following structure

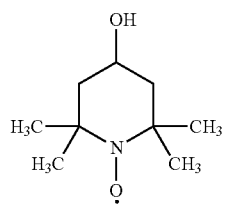

as well as pharmaceutically acceptable salts thereof.

As used herein the term "pro-drug" refers to an agent which is converted into the parent drug in vivo by some physiological chemical process (e.g., a pro-drug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the pro-drug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —C(O)$_2$H or a moiety that contains a carboxylic acid) wherein the free hydrogen is replaced by ($C_1$-$C_4$)alkyl, ($C_2$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$) alkyl.

Other exemplary pro-drugs release an alcohol of a compound of the invention wherein the free hydrogen of a hydroxyl substituent is replaced by ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyl-oxymethyl, N—($C_1$-$C_6$)alkoxycarbonylamino-methyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O($C_1$-$C_6$)alkyl)$_2$ or glycosyl (the radical resulting from detachment of the hydroxyl of the hemiacetal of a carbohydrate).

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkenyl" as used herein means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" as used herein means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "arylalkoxy" as used herein means an aryl group, as defined herein, appended to the parent molecular moiety through an alkoxy group, as defined herein. The term "heteroalkoxy" as used herein means a heteroaryl group, as defined herein, appended to the parent molecular moiety through an alkoxy group, as defined herein. Representative examples of arylalkoxy include, but are not limited to, 2-chlorophenylmethoxy.

The term "arylalkoxy" or "arylalkyloxy" as used herein means an arylalkyl group, as defined herein, appended to the parent molecular moiety through an oxygen. The term "heteroarylalkoxy" as used herein means a heteroarylalkyl group, as defined herein, appended to the parent molecular moiety through an oxygen.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The terms "arylalkyl" or "aralkyl" as used herein mean an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "alkylene," is art-recognized, and as used herein pertains to a bidentate moiety obtained by removing two hydrogen atoms of an alkyl group, as defined above.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The terms "alkylcarbonyloxy" and "arylcarbonyloxy" as used herein mean an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein means an alkyl group, as defined herein, appended to the parent molecular moiety through a sulfur atom. Representative examples of alkylthio include, but are not limited, methylthio, ethylthio, tert-butylthio, and hexylthio. The terms "arylthio," "alkenylthio" and "arylakylthio," for example, are likewise defined.

The term "amido" as used herein means —NHC(=O)—, wherein the amido group is bound to the parent molecular moiety through the nitrogen. Examples of amido include alkylamido such as $CH_3C(=O)N(H)$— and $CH_3CH_2C(=O)N(H)$—.

The term "amino" as used herein refers to radicals of both unsubstituted and substituted amines appended to the parent molecular moiety through a nitrogen atom. The two groups are each independently hydrogen, alkyl, alkylcarbonyl, alkylsulfonyl, arylcarbonyl, or formyl. Representative examples include, but are not limited to methylamino, acetylamino, and acetylmethylamino.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicylic aromatic rings. For example, bicyclic aromatic rings containing heteroatoms in a hydrocarbon ring structure are referred to as bicyclic heteroaryl rings.

The term "aryl," as used herein means a phenyl group or a naphthyl group. The aryl groups of the present invention can be optionally substituted with 1, 2, 3, 4 or 5 substituents independently selected from the group consisting of alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "arylene," is art-recognized, and as used herein pertains to a bidentate moiety obtained by removing two hydrogen atoms of an aryl ring, as defined above.

The term "arylalkylthio" as used herein means an arylalkyl group, as defined herein, appended to the parent molecular moiety through an sulfur. The term "heteroarylalkylthio" as used herein means an heteroarylalkyl group, as defined herein, appended to the parent molecular moiety through an sulfur.

The term "arylalkenyl" as used herein means an aryl group, as defined herein, appended to the parent molecular moiety through an alkenyl group. A representative example is phenylethylenyl.

The term "arylalkynyl" as used herein means an aryl group, as defined herein, appended to the parent molecular moiety through an alkynyl group. A representative example is phenylethynyl.

The term "arylcarbonyl" as used herein means an aryl group, as defined herein, appended to the parent molecular moiety through a carbonyl group, as defined herein. Representative examples of arylcarbonyl include, but are not limited to, benzoyl and naphthoyl.

The term "arylcarbonylalkyl" as used herein means an arylcarbonyl group, as defined herein, bound to the parent molecule through an alkyl group, as defined herein.

The term "arylcarbonylalkoxy" as used herein means an arylcarbonylalkyl group, as defined herein, bound to the parent molecule through an oxygen.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen.

The term "carbonyl" as used herein means a —C(=O)— group.

The term "carboxy" as used herein means a —$CO_2H$ group.

The term "cycloalkyl" as used herein means monocyclic or multicyclic (e.g., bicyclic, tricyclic, etc.) hydrocarbons containing from 3 to 12 carbon atoms that is completely saturated or has one or more unsaturated bonds but does not amount to an aromatic group. Examples of a cycloalkyl group include cyclopropyl, cyclobutyl, cyclopentyl, cyclopentenyl, cyclohexyl and cyclohexenyl.

The term "cycloalkoxy" as used herein means a cycloalkyl group, as defined herein, appended to the parent molecular moiety through an oxygen.

The term "cyano" as used herein means a —CN group. The term "formyl" as used herein means a —C(=O)H group. The term "halo" or "halogen" means —Cl, —Br, —I or —F.

The term "haloalkoxy" as used herein means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocyclyl", as used herein include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroaryl" as used herein include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroarylene," is art-recognized, and as used herein pertains to a bidentate moiety obtained by removing two hydrogen atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "hydroxy" as used herein means an —OH group.

The term "hydroxyalkyl" as used herein means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein means a —SH group.

The term "nitro" as used herein means a —NO$_2$ group.

The term "phosphinyl" as used herein includes derivatives of the H$_3$P— group, wherein the hydrogens are independently replaced with alkyl, adamantyl, fluoroalkyl, cycloalkyl, aryl, heteroaryl, heterocycyl, aryloxy, or heteroaryloxy groups.

The term "silyl" as used herein includes hydrocarbyl derivatives of the silyl (H$_3$Si—) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl.

The term "silyloxy" as used herein means a silyl group, as defined herein, is appended to the parent molecule through an oxygen atom.

The definition of each expression, e.g., alkyl, m, n, and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

EXEMPLIFICATION

The invention now being generally described, it will be more readily understood by reference to the following, which is included merely for purposes of illustration of certain aspects and embodiments of the present invention, and is not intended to limit the invention.

Chemical Synthesis of Tempol/Telmisartan Ester-Linked Adduct

Analytical Methods. NMR spectra were recorded using a Varian-400 spectrometer for $^1$H (400 MHz). Chemical shifts (δ) are given in ppm downfield from tetramethylsilane, as internal standard, and coupling constants (J-values) are in hertz (Hz). Purifications by flash chromatography were performed. Liquid chromatography/mass spectrometry (LC/MS) analyses were conducted using Shimadzu LC-20AD pumps and a SPD-20A UV-vis detector. High-resolution mass spectra (HMRS) were recorded on a QSTAR Elite mass spectrometer.

Telmisartan Extraction. Telmisartan tablets were triturated, suspended in methanol and stirred for about 20 mins. Filtered off the solid, the methanol solution was concentrated, and the residue was purified by chromatography to afford white solid in 90% yield. $^1$H NMR (CDCl$_3$, 400 MHz) δ 8.38 (m, 1H), 8.02 (dd, 1H, J=1.2, 1.2 Hz), 7.39 (m, 8H), 7.17 (s, 1H), 7.15 (s, 1H), 7.04 (s, 1H), 6.95 (s, 1H), 5.40 (s, 2H), 3.74 (s, 3H), 3.13 (t, 2H, J=7.6, 8.0 Hz), 2.69 (s, 3H), 1.99 (m, 2H), 1.15 (t, 3H, J=7.6, 7.2 Hz).

Conjugated Telmisartan with Tempol (YK-4-250).

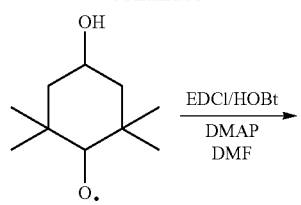

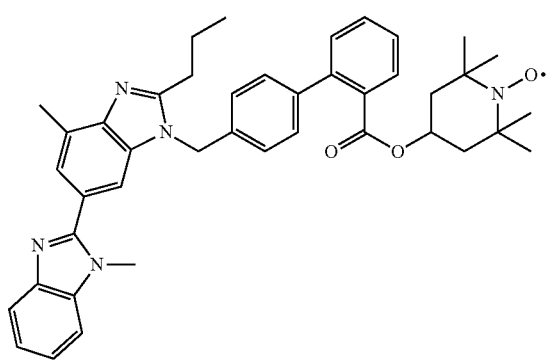

YK-4-250

To an ice bath cooled solution of telmisartan (0.8 g, 1.55 mmol) in DMF (50 mL) was added 1-hydroxybenzotriazole (HOBt, 0.25 g, 1.87 mmol), 4-dimethylamino pyridine (DMAP, 0.23 g, 1.87 mmol), and 1-(3-dimethylaminopropyl)-3-ethylcarbodiimide hydrochloride (EDCI, 0.39 g, 2.02 mmol), followed by tempol (0.29 g, 1.712 mmol). The mixture was stirred at room temperature for 48 h. Water (15 mL) was added to the mixture and stirred at room temperature for 10 minutes. The mixture was extracted with ethyl acetate (3×15 mL). The organic layer was washed with sat. LiCl (15 mL), sat. NaHCO$_3$ (15 mL), water (15 mL) and brine (15 mL), dried over Na$_2$SO$_4$. The solvent was evaporated and the residue was purified by flash chromatography using CH$_2$Cl$_2$-MeOH to afford YK-4-250 as a pink soft solid (0.81 g, 78%). LC-MS (ESI): m/z 669 (M+H)$^+$; HRMS (TOF): calculated for C$_{42}$H$_{47}$N$_5$O$_3$ (M+H)$^+$: 669.3679; Found: 669.3578.

Conjugated Telmisartan with Tempamine (PLJ-Tempamsartan).

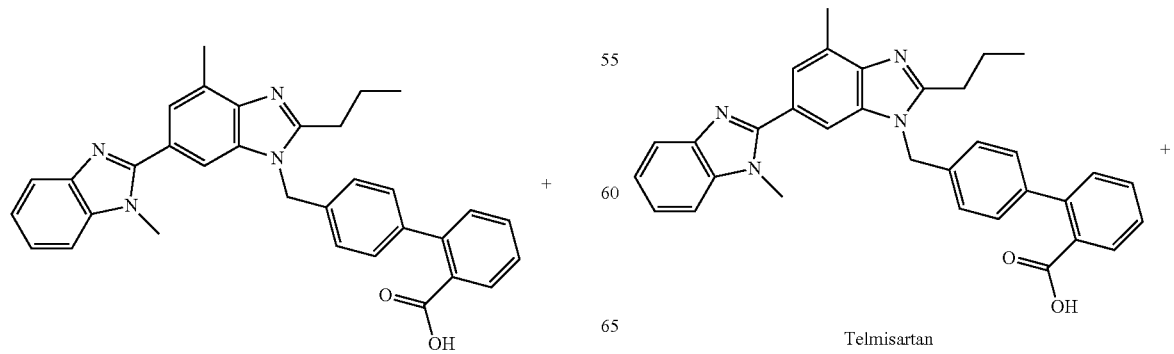

Telmisartan

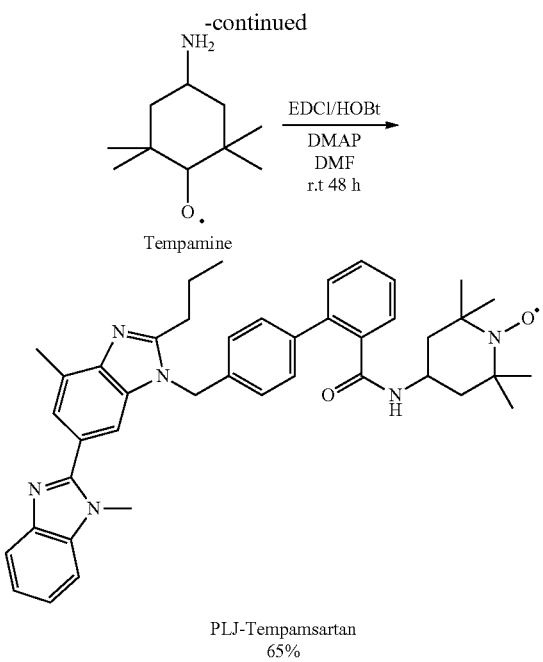

PLJ-Tempamsartan
65%

Into a 250 mL two-neck round bottom flask fitted with a nitrogen-filled balloon and magnetic stirrer was added 100 mL of anhydrous DCM. The solvent cooled in an ice bath for 5 min before adding telmisartan (500 mg, 0.972 mmol), HOBt (131 mg, 0.972 mmol), DAMP (119 mg, 0.972 mmol), and EDCI-HCl (186 mg, 0.972 mmol), followed by 4-amino-2,2,6,6-tetramethypiperidine-N-oxyl (tempamine) (166 mg, 0.972 mmol). The mixture stirred for 48 h under nitrogen at room temperature. Before work-up, fresh DCM (30 mL) was added to the reaction mixture. The mixture was washed with $NaHCO_3$ (sat., aq.) (50 mL), water (50 mL), and brine (50 mL). The organic phase was dried over $Na_2SO_4$ and filtered. The solvent was evaporated and the pink residue was purified by Biotage using EtOAc/MeOH. Gradient: (1) 0%-1%, 5 CV; (2) 1%-1%, 15 CV; (3) 1%-5%, 5 CV. Fractions yielded a light pink crystalline solid (310 mg, 62%), m.p. 229-230° C. Molecular weight: 667.86.

Isolation of Preglomerular Vascular Smooth Muscle Cells

Preglomerular vascular smooth muscle cells (PGVSMCs) were isolated from 13- to 15-week-old male spontaneously hypertensive rats purchased from Taconic Farms (Germantown, N.Y.) as previously described (3, 9). Briefly, 1% $Fe_2O_3$ in DMEM was injected into isolated kidneys through the renal artery. The iron-loaded kidney was removed from the rat, the cortex was minced and washed in a 1% collagenase IV solution. Blood vessels were collected on a magnet and incubated with DMEM/F12 supplemented with 10% FCS and 20 U of penicillin-streptomycin. Experiments were conducted between passage 5 and 15. PGVSMCs were cultured in DMEM/F12 supplemented with 10% FBS, 100 U/mL penicillin, 100 µg/mL streptomycin and 200 µg/mL glutamine at 37° C. in 5% $CO_2$-95% air at 98% humidity. The VSCM phenotype was confirmed by characteristic morphology (hill-and-valley pattern), contraction to norepinephrine and Ang II, expression of smooth muscle-specific alpha-actin and the absence of von Willebrand factor (9).

Superoxide Detection in Vitro

Figure 1:
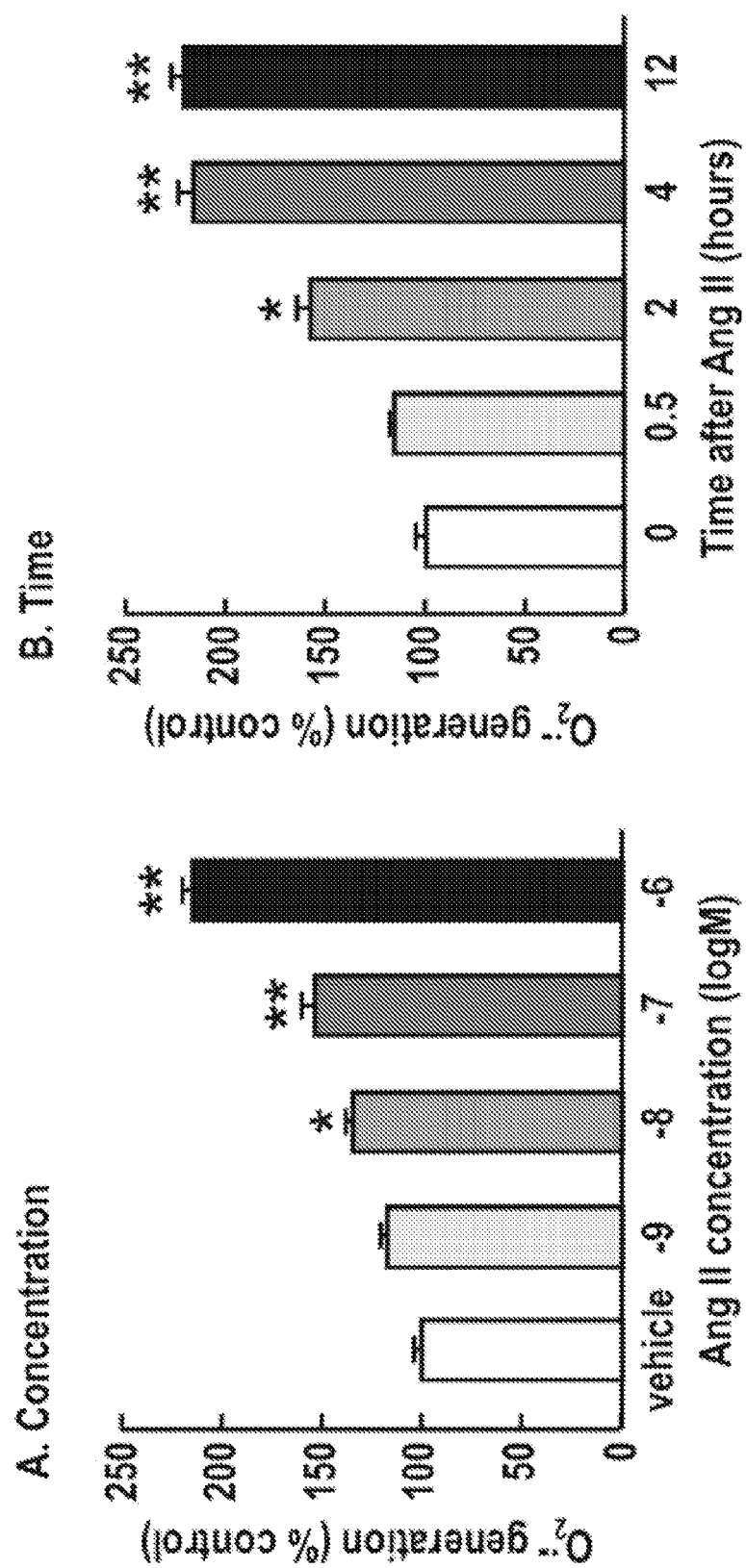
FIG. 1 is a pair of graphs depicting mean±standard error of the mean (SEM) values (n=3) for $O_2.^-$ generation by preglomerular vascular smooth muscle cells (PGVSMCs) from spontaneously hypertensive rats stimulated for 4 hours with graded doses of angiotensin II (panel A) or for graded times with $10^{-6}$ M Ang II (panel B). Compared to vehicle: *, $p<0.05$; **, $p<0.01$.

Low dose (10 µmol $L^{-1}$) lucigenin-enhanced chemiluminescence was used as previously described, to detect $O_2.^-$, antioxidants or SOD mimetic properties. Vehicle or drugs ($10^{-4}$ M) were first added to cell-free buffer with $O_2.^-$ stimulated with xanthine (25 µmol/L) plus xanthine oxidase (9 IU/mL) to study the intrinsic antioxidant properties of the drugs used (34). Subsequent studies were performed in PGVSMCs from spontaneously hypertensive rats grown in 6-well plates. Cells ($10^6$ cells per well) were stimulated for 4 hours with Ang II ($10^{-6}$ M) to generate $O_2.^-$ in the presence of vehicle or drugs (19, 34, 45). This dose and time interval for Ang II were selected after preliminary studies showed that $10^{-6}$ M Ang II doubled $O_2.^-$ generation and that this was maximal at 4 hours (FIG. 1).

To determine the effects of drugs, cells were pretreated with graded concentrations ($10^{-12}$ to $10^{-4}$ M) of tempol, telmisartan, tempol plus telmisartan, and tempol/telmisartan ester-linked adduct or vehicle (PBS) for 2 hours. Thereafter, they were co-incubated with $10^{-6}$ M Ang II for 4 hours in serum-free DMEM/F-12 medium, washed twice with assay buffer (130 mM NaCl, 5 mM KCl, 1 mM $MgCl_2$, 1 mM $CaCl_2$, 35 mM phosphoric acid, and 20 mM HEPES, pH 7.4) and scraped into an assay tube. Chemiluminescence was quantitated in a reader (AutoLumatPlus LB 953; EG&G, Berthold, Germany). The dynamic tracing was recorded for 180 seconds after the addition of lucigenin (10 µmol·$L^{-1}$) and NADPH (100 µmol·$L^{-1}$). Arbitrary light units (ALUs) were corrected for the protein concentration and duration of the experiment (ALU/second/per milligram of protein). Assays were performed in triplicate. The protein concentrations were measured with Bio-Rad kit (Hercules, Calif.). Data are presented as percentage reductions in chemiluminescence counts, relative to vehicle, by graded doses of each drug.

Angiotensin Type 1 and 2 Receptor Binding Displacement

Angiotensin II, Type 1 Assay.

Frozen human KAN-TS cells were thawed, diluted with assay buffer, homogenized, and stored on ice until addition to assay tubes. Angiotensin II, Type I (Human) assay was performed using a norvacreen method (CAT #: AT1-100 (Lot #: 75)). A Kd: [$^{125}$I]-Tyr4, Ile8-Angiotensin II=0.2 nM with a Bmax (Receptor density): 0.11 µmol/mg protein at an AT1 protein concentration of 8 mg/vial was used as a control. Briefly, the membranes were suspended in 50 mM TRIS-HCl containing 10% glycerol, 100 mM NaCl, 1 mM $MgCl_2$, 0.1% BSA, 0.1 mM and bacitracin (pH 7.2 at 25° C.) in a vial of 1.5 mL. The assay incubation was 180 minutes at 25° C. Filters: GF/B filters were used pre-soaked in 0.1% PEI and a wash buffer (wash 5 times with 1 mL per tube) of 50 mM NaCl.

Angiogensin II, Type 2 Assay.

The assay was performed with a membrane preparation from bovine cerebellum. 200 µL of receptor suspension was re-suspended as 400 units in 80 mL and 100 units in 20 mL. The ligand [$^{125}$I]Tyr-4-Angiotensin II ([M] 1E-$^{10}$, Kd (binding affinity) 4E-$^{10}$, Bmax 2.11 fmol/mg) was used as a control. Radioactivity was counted in DPM. The assay buffer was 50 mM TRIS-HCl, containing 100 mM NaCl, 1 mM $MgCl_2$, 0.1 mM Bacitracin, 0.1% BSA, (pH 7.2 at 25° C.) in an assay volume of 250 µL. Radioligand: 25 µL of Sar1, Tyr4-[$^{125}$I].

Measuring Antihypertensive Response in Spontaneously Hypertensive Rats

Spontaneously hypertensive rats (SHR) were anesthetized with 3% isoflurane for placement of telemetric blood pressure recorders as described (46). After 10 days, spontaneously hypertensive rats were anesthetized with halothane between 9 and 10 am and given a 2 mL gavage. Each rat was first given a training gavage with 2 mL of vehicle (0.9% w/v sodium chloride) and, two days later a second vehicle gavage as the control group. We detected no differences in the pattern of 4-hourly BP recording after the first or second vehicle gavage, compared to a day in which no gavage was given (data not shown). Blood pressure was recorded continuously. Data are presented as mean values over 4-hr periods for mean arterial pressure (MAP) and heart rate (HR). Two days after the second vehicle gavage, rats were again anesthetized with halothane and given a 2 mL gavage with one of the test drugs (10 mmol/L or 80 µmol·kg$^{-1}$). In random order rats received tempol, telmisartan, tempol plus telmisartan, or tempol/telmisartan ester-linked adduct (YK). Each rat received only one drug or drug combination. Two additional groups were tested similarly with candesartan and tempol+candesartan.

Figure 2:
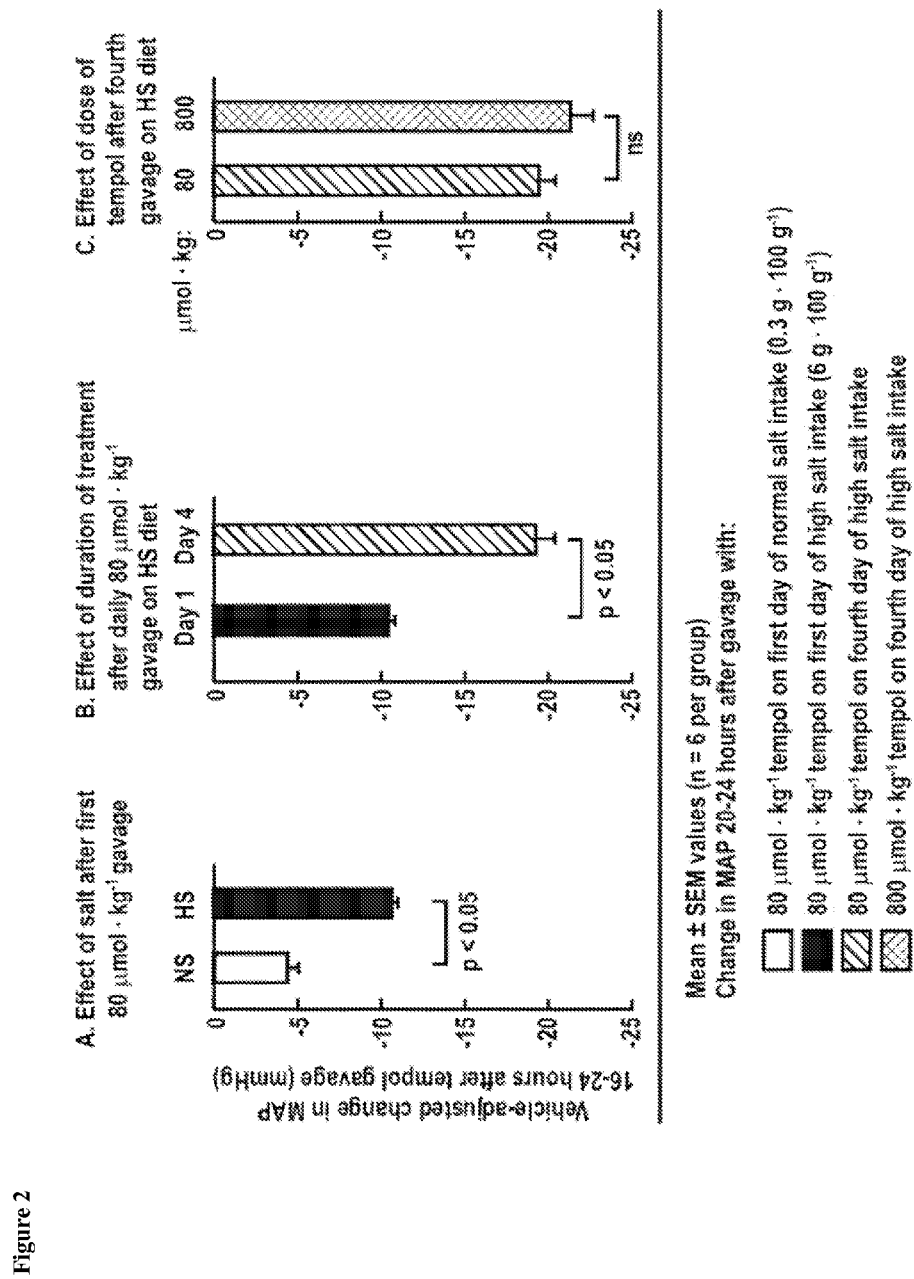
FIG. 2 is a series of three graphs depicting the results of pilot studies in conscious spontaneously hypertensive rats relating vehicle-adjusted changes in the mean arterial pressure at 16-24 hours after gavage with tempol. Panel A contrasts the changes after one dose of tempol during normal salt (0.3 g·100 g$^{-1}$) compared to high salt (6 g·100 g$^{-1}$). Panel B contrasts responses of spontaneously hypertensive rats on high salt diet to the first and the fourth gavage with tempol.

Preliminary studies were undertaken of antihypertensive responsiveness to gavage with 80 and 800 µmol kg$^{-1}$ of tempol. A dose of 80 µmol kg was selected since it produced a reproducible antihypertensive response which similar to the 800 µmol·kg$^{-1}$ and therefore was considered maximal (FIG. 2). In another series of preliminary studies, the fall in MAP at the time of maximum response 16-24 hours after tempol (80 mmol kg$^{-1}$) was twice as great in spontaneously hypertensive rats equilibrated to a diet containing a high salt content (6 g·100 g$^{-1}$) compared to a normal salt (0.3 g·100 g$^{-1}$). In another pilot study, the fall in MAP in spontaneously hypertensive rats receiving a high salt intake was twice as great after 4 daily doses of tempol, compared to the response to the first dose. Therefore, the study was conducted in rats equilibrated to a high salt intake (Teklad Inc, 2826 Latham Drive, Madison, Wis. 53713) and given four daily doses of 80 mmol kg$^{-1}$ of drugs or vehicle.

Statistical Analysis

Mean±SEM values were calculated at each concentration. Data were compared by analysis of variance (ANOVA). Where appropriate, a post-hoc student's t test was used to assess differences between drugs. Significance was taken at p<0.05.

Results

To assess the interaction of telmisartan and tempol/telmisartan ester-linked adduct with AT1- and AT2-receptors, radioligand binding studies were undertaken (FIG. 3). It was concluded that tempol/telmisartan ester-linked adduct retains the full AT1-R displacement activity of telmisartan without effects on AT2-R binding.

To assess the intrinsic antioxidant activity of each compound, drugs (10$^{-4}$M) were added to a cell-free buffer system containing xanthine plus xanthine oxidase. Tempol, tempol+ telmisartan, tempol/telmisartan ester-linked adduct, and oxypurinol (inhibitor of xanthine oxidase) inhibited lucigenin-enhanced chemiluminescence counts by 60-75% whereas telmisartan was ineffective (FIG. 4). It was concluded that tempol is a direct-acting SOD mimetic antioxidant. It retains its full SOD mimetic activity when mixed with, or complexed to, telmisartan. Telmisartan lacks intrinsic antioxidant activity.

As compared to vehicle, all drugs caused a dose-dependent inhibition of $O_2^-$ generation in Ang II-stimulated spontaneously hypertensive rats PGVSMCs. Tempol+telmisartan (FIG. 5A) and tempol/telmisartan ester-linked adduct (FIG. 5B) were significantly more effective than tempol or telmisartan alone at both ends of the dose response curve at 10$^{-11}$, 10$^{-10}$ and 10$^{-6}$ M. There were no significant differences between tempol+telmisartan and tempol/telmisartan ester-linked adduct at any concentration tested. There were no significant differences between the effect of tempol and telmisartan up to 10$^{-4}$M where tempol was significantly (p<0.05) more effective than telmisartan. It was therefore concluded that tempol plus telmisartan and tempol/telmisartan ester-linked adduct have greater effectiveness for inhibition of $O_2^-$ generation at several points in the dose-response curves than either drug alone. Indeed, the effectiveness of tempol+telmisartan and tempol/telmisartan ester-linked adduct at 10$^{-11}$M is comparable to tempol alone at 10$^{-9}$ M and telmisartan at 10$^{-8}$ M, suggesting that the combination of the tempol/telmisartan ester-linked adduct increases the sensitivity to metabolism of $O_2^-$ by 100-1000 fold.

In addition, it was found that tempol, telmisartan, candesartan and tempol/telmisartan ester-linked adduct reduced the MAP of conscious spontaneously hypertensive rats. The effects were maximal after 16-24 hours after each gavage (FIG. 6). Data in FIG. 8 gives absolute values for MAP and HR before and 16-24 hours after the first or the fourth daily gavage. Vehicle-adjusted changes are shown in FIG. 7.

Telmisartan and candesartan were significantly more effective in reducing the BP than tempol after the first and the fourth gavage. At 12-24 hours after the first gavage, tempol+ telmisartan and tempol/telmisartan ester-linked adduct were more effective than either tempol or telmisartan and tempol+ candesartan was more effective than tempol or candesartan. This additive effect of the ARB and tempol, or of the tempol/ telmisartan ester-linked adduct, on BP was lost with repeated dosing, as shown by the similar BP changes with tempol+ ARB to the ARB alone 16-24 hours after the fourth gavage (FIGS. 7 and 8).

In another experiment, conscious salt-loaded spontaneously hypertensive rats received daily oral gavage with 2 mL of 10 mmol/L tempol, telmisartan, tempol/telmisartan ester-linked adduct (YK), tempamine/telmisartan amide-linked adduct (PLJ), and tempol+telmisartan. The drugs were dissolved in DMSO. The mean vehicle-adjusted fall in MAP over three days (n=3 for each group) were as shown in Table 1:

TABLE 1

| Drug | Δ MAP (mmHg) Day 1 | Δ MAP (mmHg) Day 2 | Δ MAP (mmHg) Day 3 |
|---|---|---|---|
| Tempol | 0 | −4 | −2 |
| Telmisartan | −14 | −20 | −16 |
| YK | −13 | −14 | −14 |
| PLJ | −13 | −14 | −14 |
| Tempol + Telmisartan | −17 | −13 | −14 |

The results shown in Table 1 indicate that both YK and PLJ reduce blood pressure of conscious SHR similar to telmisartan. The apparent absence of any consistent effect of tempol, or of any additional effect of tempol+telmisartan over telmisartan alone in this experiment suggests that the DMSO vehicle used to dissolve the drugs inactivated the nitroxide action, but this still left a consistent anti-hypertensive effect of YK and PLJ. For this reason, it may be desirable to exclude DMSO from a pharmaceutical composition of the invention.

REFERENCES

The following references correspond to the numbers above in parenthesis. All of these references are incorporated by reference in their entirety. In addition, all of the U.S. patents and U.S. published patent applications cited herein are hereby incorporated by reference.

1. Results of MRC hypertension trial. *Lancet* July 13: 92-93, 1985.
2. Treatment of hypertension in the over-60s. *Lancet* 1: 1369-1370, 1985.
3. Andresen B T, Jackson E K, Romero G G. Angiotensin II signaling to phospholipase D in renal microvascular smooth muscle cells in SHR. *Hypertens* 37: 635-639, 2001.

4. Bakris G, Burgess E, Weir M, Davidai G, Koval S. Telmisartan is more effective than losartan in reducing proteinuria in subjects with diabetic nephropathy. *Kidney Int* 74: 364-369, 2008.
5. Battershill A J, Scott U. Telmisartan: a review of its use in the management of hypertension. *Drugs* 66: 51-83, 2006.
6. Benson S C, Pershadsingh H A, Ho C I, Chittiboyina A, Desai P, Pravenec M, Qi N, Wang J, Avery M A, Kurtz T W. Identification of telmisartan as a unique angiotensin II receptor antagonist with selective PPARgamma-modulating activity. *Hypertens* 43: 993-1002, 2004.
7. Brenner B M, Cooper M E, de Zeeuw D, Keane W F, Mitch W E, Parving H H, Remuzzi G, Snapinn S M, Zhang Z, Shahinfar S. Effects of losartan on renal and cardiovascular outcomes in subjects with type 2 diabetes and nephropathy. *N Engl J Med* 345: 861-869, 2001.
8. Chobanian A V, Bakris G L, Black H R, Cushman W C, Green L A, Izzo J L, Jr., Jones D W, Materson B J, Oparil S, Wright J T, Jr., Roccella E J. The Seventh Report of the Joint National Committee on Prevention, Detection, Evaluation, and Treatment of High Blood Pressure: the JNC 7 report. *JAMA* 289: 2560-2572, 2003.
9. Dubey R K, Roy A, Overbeck H W. Culture of renal arteriolar smooth muscle cells. Mitogenic responses to angiotensin II. *Circ Res* 71: 1143-1152, 1992.
10. Grassi G, Quarti-Trevano F, Mancia G. Cardioprotective effects of telmisartan in uncomplicated and complicated hypertension. *J Renin Angiotensin Aldosterone Syst* 9: 66-74, 2008.
11. Guo P, Nishiyama A, Rahman M, Nagai Y, Noma T, Namba T, Ishizawa M, Murakami K, Miyatake A, Kimura S, Mizushige K, Abe Y, Ohmori K, Kohno M. Contribution of reactive oxygen species to the pathogenesis of left ventricular failure in Dahl salt-sensitive hypertensive rats: effects of angiotensin II blockade. *J Hypertens* 24: 1097-1104, 2006.
12. Harrison D, Gongora M C, Guzik T J, Widder J. Oxidative stress and/or hypertension. *Hypertens* 1: 30-44, 2007.
13. Hinoi T, Tomohiro Y, Kajiwara S, Matsuo S, Fujimoto Y, Yamamoto S, Shichijo T, Ono T. Telmisartan, an angiotensin II type 1 receptor blocker, improves coronary microcirculation and insulin resistance among essential hypertensive subjects without left ventricular hypertrophy. *Hypertens Res* 31: 615-622, 2008.
14. Hollenberg N K. The kidney and angiotensin-converting enzyme inhibitors, angiotensin receptor blockers, and aldosterone antagonists. In: *Therapy in Nephrology and Hypertension*, edited by Brady H R and Wilcox C S. Philadelphia, Pa.: W.B. Saunders/Elsevier, Inc., 2003, p. 547-554.
15. Hsueh W A, Bruemmer D. Peroxisome proliferator-activated receptor gamma: implications for cardiovascular disease. *Hypertens* 43: 297-305, 2004.
16. Imayama I, Ichiki T, Inanaga K, Ohtsubo H, Fukuyama K, Ono H, Hashiguchi Y, Sunagawa K. Telmisartan downregulates angiotensin II type 1 receptor through activation of peroxisome proliferator-activated receptor gamma. *Cardiovasc Res* 72: 184-190, 2006.
17. Julius S, Nesbitt S D, Egan B M, Weber M A, Michelson E L, Kaciroti N, Black H R, Grimm R H, Jr., Messerli F H, Oparil S, Schork M A. Feasibility of treating prehypertension with an angiotensin-receptor blocker. *N Engl J Med* 354: 1685-1697, 2006.
18. Kirkby N S, Hadoke P W, Bagnall A J, Webb D J. The endothelin system as a therapeutic target in cardiovascular disease: great expectations or bleak house? *Br J Pharmacol* 153: 1105-1119, 2008.
19. Kitiyakara C, Chabrashvili T, Chen Y, Blau J, Karber A, Aslam S, Welch W J, Wilcox C S. Salt intake, oxidative stress and renal expression of NADPH oxidase and superoxide dismutase. *J Am Soc Nephrol* 14: 2775-2782, 2003.
20. Kjeldsen S E, Oparil S, Narkiewicz K, Hedner T. A stunning day in hypertension research—Results of ONTARGET, ACCOMPLISH and HYVET. *blood press* 17: 68-69, 2008.
21. Klein IHHT, Lightenberg G, Oey P L, Koomans H A, Blankestijn P J. Sympathetic activity is increased in polycystic kidney disease and is associated with hypertension. *J Am Soc Nephrol* 12: 2427-2433, 2001.
22. Klein IHHT, Ligtenberg G, Oey P L, Koomans H A, Blankestijn P J. Enalapril and losartan reduce sympathetic hyperactivity in subjects with chronic renal failure. *J Am Soc Nephrol* 14: 425-430, 2003.
23. Krakoff L R. Treatment decisions for hypertension. In: *Therapy in Nephrology and Hypertension*, edited by Brady H R and Wilcox C S. Philadelphia, Pa.: W.B. Saunders/Elsevier, Inc., 2003, p. 523-530.
24. Krishna M C, Russo A, Mitchell J B, Goldstein S, Dafni H, Samuni A. Do nitroxide antioxidants act as scavengers of $O_2^-$ or as SOD mimics? *J Biol Chem* 271: 26026-26031, 1996.
25. Liang Q, Smith A D, Pan S, Tyurin V A, Kagan V E, Hastings T G, Schor N F. Neuroprotective effects of TEMPOL in central and peripheral nervous system models of Parkinson's disease. *Biochem Pharmacol* 70: 1371-1381, 2005.
26. Lindhold L H, Ibsen H, Dahlof B, Devereux R B, Beevers G, de Faire U, Fyhrquist F, Julius S, Kjeldsen S E, Kristiansson K, Lederballe-Pedersen O, Nieminen M S, Omvik P, Oparil S, Wedel H, Aurup P, Edelman J, Snapinin S Cardiovascular morbidity and mortality in subjects with diabetes in the Losartan Intervention For Endpoint reduction in hypertension study (LIFE): a randomised trial against atenolol. *Lancet* 359: 1004-1010, 2002.
27. Mann J F, Schmieder R E, McQueen M, Dyal L, Schumacher H, Pogue J, Wang X, Maggioni A, Budaj A, Chaithiraphan S, Dickstein K, Keltai M, Metsarinne K, Oto A, Parkhomenko A, Piegas L S, Svendsen T L, Teo K K, Yusuf S. Renal outcomes with telmisartan, ramipril, or both, in people at high vascular risk (the ONTARGET study): a multicentre, randomised, double-blind, controlled trial. *Lancet* 372: 547-553, 2008.
28. Mehta J L, Hu B, Chen J, Li D. Pioglitazone inhibits LOX-1 expression in human coronary artery endothelial cells by reducing intracellular superoxide radical generation. *Arterioscler Thromb Vasc Biol* 23: 2203-2208, 2003.
29. Meng S, Cason G W, Gannon A W, Racusen L C, Manning R D, Jr. Oxidative stress in Dahl salt-sensitive hypertension. *Hypertens* 41: 1346-1352, 2003.
30. Mitchell J B, Samuni A, Krishna M C, De Graff W G, Ahn M S, Samuni U, Russo A. Biologically active metal-independent superoxide dismutase mimetics. *Biochem* 29: 2802-2807, 1990.
31. Mitchell J B, Xavier S, DeLuca A. M., Sowers A L, Cook J A, Krishna M C, Hahn S M, Russo A. A low molecular weight antioxidant decreases weight and lowers tumor incidence. *Free Rad Biol Med* 34: 93-102, 2003.
32. Oeckler R A, Kaminski P M, Wolin M S. Stretch enhances contraction of bovine coronary arteries via an NAD (P) oxidase-mediacted activation of the extracellular signal-regulated kinase mitogen-activated protein kinase cascade. *Cir Res* 92: 24-31, 2003.
33. Ogihara T, Asano T, Ando K, Chiba Y, Sakoda H, Anai M, Shojima N, Ono H, Onishi Y, Fujishiro M, Katagiri H, Fukushima Y, Kikuchi M, Noguchi N, Aburatani H, Komuro I, Fujita T. Angiotensin II-induced insulin resistance is associated with enhanced insulin signaling. *Hypertens* 40: 872-879, 2002.

34. Patel K, Chen Y, Dennehy K, Blau J, Mendonca M, Tarpey M, Krishna M, Mitchell J B, Welch W J, Wilcox C S. Acute antihypertensive action of nitroxides in the spontaneously hypertensive rat. *Am J Physiol Regul Integr Comp Physiol* 290: R37-R43, 2006.

35. Polikandriotis J A, Mazzella L J, Rupnow H L, Hart C M. Peroxisome proliferator-activated receptor gamma ligands stimulate endothelial nitric oxide production through distinct peroxisome proliferator-activated receptor gamma-dependent mechanisms. *Arterioscler Thromb Vasc Biol* 25: 1810-1816, 2005.

36. Rugenenti P, Perna A, Gherardi G, Gaspari F, Benini R, Remuzzi G. Renal function and requirement for dialysis in chronic nephropathy subjects on long-term ramipril: REIN follow-up trial. *The Lancet* 352: 1252-1256, 1998.

37. San Martin A, Du P, Dikalova A, Lassegue B, Aleman M, Gongora M C, Brown K, Joseph G, Harrison D G, Taylor W R, Jo H, Griendling K. Reactive oxygen species-selective regulation of aortic inflammatory gene expression in type 2 diabetes. *Am J Physiol Heart Circ Physiol* 292: H2073-H2082, 2007.

38. Scalera F, Martens-Lobenhoffer J, Bukowska A, Lendeckel U, Tager M, Bode-Boger S M. Effect of telmisartan on nitric oxide—asymmetrical dimethylarginine system: role of angiotensin II type 1 receptor gamma and peroxisome proliferator activated receptor gamma signaling during endothelial aging. *Hypertens* 51: 696-703, 2008.

39. Schnackenberg C, Wilcox C S. Two-week administration of tempol attenuates both hypertension and renal excretion of 8-Isoprostaglandin $F_{2\alpha}$. *Hypertens* 33: 424-428, 1999.

40. Schnackenberg C G, Welch W J, Wilcox C S. Normalization of blood pressure and renal vascular resistance in SHR with a membrane-permeable superoxide dismutase mimetic: role of nitric oxide. *Hypertens* 32: 59-64, 1998.

41. Schupp M, Janke J, Clasen R, Unger T, Kintscher U. Angiotensin type 1 receptor blockers induce peroxisome proliferator-activated receptor-gamma activity. *Circ* 109: 2054-2057, 2004.

42. Teerlink T, Nijveldt R J, de J S, Van Leeuwen P A. Determination of arginine, asymmetric dimethylarginine, and symmetric dimethylarginine in human plasma and other biological samples by high-performance liquid chromatography. *Anal Biochem* 303: 131-137, 2002.

43. Thiemermann C. Membrane-permeable radical scavengers (tempol) for shock, ischemia-reperfusion injury, and inflammation. *Crit. Care Med* 31: S76-S84, 2003.

44. Wanby P, Teerlink T, Brudin L, Brattstrom L, Nilsson I, Palmqvist P, Carlsson M. Asymmetric dimethylarginine (ADMA) as a risk marker for stroke and TIA in a Swedish population. *Atherosclerosis* 185: 271-277, 2006.

45. Welch W J, Chabrashvili T, Solis G, Chen Y, Gill P, Aslam S, Wang X, Ji H, Sandberg K, Jose P, Wilcox C S. Role of extracellular superoxide dismutase in the mouse angiotensin slow pressor response. *Hypertens* 48: 934-941, 2006.

46. Welch W J, Mendonca M, Blau J, Karber A, Dennehy K, Lao Y, Jose P, Wilcox C S. Antihypertensive response to prolonged tempol in the spontaneously hypertensive rat. *Kidney Int* 68: 179-187, 2005.

47. Welch W J, Patel K, Modlinger P, Mendonca M, Kawada N, Dennehy K, Aslam S, Wilcox C S. Roles of vasoconstrictor prostaglandins, COX-1 and -2, AT1, AT2 and TP receptors in a rat model of early 2K, 1C hypertension. *Am J Physiol* 293: H2644-H2649, 2007.

48. Wilcox C S. Oxidative stress and nitric oxide deficiency in the kidney: a critical link to hypertension? *Am J Physiol Regul Integr Comp Physiol* 289: R913-R935, 2005.

49. Wilcox C S. Nitric oxide synthase and cyclooxygenase in the kidneys. In: *Principles of Molecular Medicine*, edited by Runge M S and Patterson C. Totowa: Humana Press, 2006, p. 606-612.

50. Wilcox C S, Pearlman A. Chemistry and antihypertensive effects of tempol and other nitroxides. *Pharm Rev* 60: 418-469, 2008.

51. Wright J T, Jr., Dunn J K, Cutler J A, Davis B R, Cushman W C, Ford C E, Haywood U, Leenen F H, Margolis K L, Papademetriou V, Probstfield J L, Whelton P K, Habib G B. Outcomes in hypertensive black and nonblack subjects treated with chlorthalidone, amlodipine, and lisinopril. *JAMA* 293: 1595-1608, 2005.

52. Yamada S, Ano N, Toda K, Kitaoka A, Shiono K, Inoue G, Atsuda K, Irie J. Telmisartan but not candesartan affects adiponectin expression in vivo and in vitro. *Hypertens Res* 31: 601-606, 2008.

53. Yoshida T, Yamagishi S, Nakamura K, Matsui T, Imaizumi T, Takeuchi M, Koga H, Ueno T, Sata M. Telmisartan inhibits AGE-induced C-reactive protein production through downregulation of the receptor for AGE via peroxisome proliferator-activated receptor-gamma activation. *Diabetologia* 49: 3094-3099, 2006.

54. Yusuf S, Teo K K, Pogue J, Dyal L, Copland I, Schumacher H, Dagenais G, Sleight P, Anderson C. Telmisartan, ramipril, or both in subjects at high risk for vascular events. *N Engl J Med* 358: 1547-1559, 2008.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

We claim:
1. A compound of formula I:

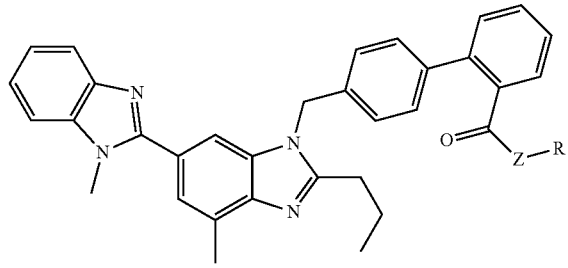

or a pharmaceutically acceptable salt thereof, wherein Z is —O— or —N(H)—; and

R is

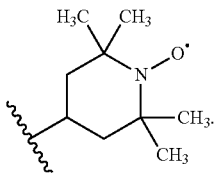

2. The compound of claim 1, wherein Z is —O—.
3. The compound of claim 1, wherein Z is —N(H)—.
4. A pharmaceutical composition, comprising a compound of claim 1, and a pharmaceutically acceptable carrier.
5. A method of treating oxidative stress and/or hypertension in a subject, comprising the step of administering a therapeutically effective amount of a compound of claim 1.

* * * * *